United States Patent [19]

Fujii et al.

[11] 4,267,102
[45] May 12, 1981

[54] BLEOMYCIN GROUP ANTIBIOTICS

[75] Inventors: Akio Fujii, Kamakura; Takeyo Fukuoka, Tokyo; Yasuhiko Muraoka, Kitamoto; Tomohisa Takita, Asaka; Hamao Umezawa, Tokyo, all of Japan

[73] Assignee: Nippon Kayaku Kabushiki Kaisha, Tokyo, Japan

[21] Appl. No.: 126,123

[22] Filed: Feb. 29, 1980

[30] Foreign Application Priority Data

Mar. 5, 1979 [JP] Japan .................................. 54-24555
Mar. 5, 1979 [JP] Japan .................................. 54-24556

[51] Int. Cl.³ .................... C07C 103/52; A61K 37/00
[52] U.S. Cl. .............................. 260/112.5 R; 424/177
[58] Field of Search ................ 260/112.5 R; 424/177; 536/17 R

[56] References Cited

U.S. PATENT DOCUMENTS

| 3,843,448 | 10/1974 | Umezawa et al. | 260/112.5 R |
| 3,846,400 | 11/1974 | Umezawa et al. | 260/112.5 R |
| 3,922,262 | 11/1975 | Umezawa et al. | 260/112.5 R |
| 3,929,993 | 12/1975 | Takita et al. | 260/112.5 R |
| 4,195,018 | 3/1980 | Takita et al. | 260/112.5 R |

FOREIGN PATENT DOCUMENTS 2828833 1/1979 Fed. Rep. of Germany .... 260/112.5 R

OTHER PUBLICATIONS

Umezawa, H., et al., J. Antibiotics, vol. 29, pp. 200-215, (1966).
Argoudelis, A., et al., J. Antibiotics, vol. 24, pp. 543-557 (1971).
Umezawa, H., et al., J. Antibiotics, vol. 25, pp. 409-420, (1972).
Umezawa, H., et al., J. Antibiotics, vol. 27, pp. 419-424, (1974).
Kawamoto, I., et al., J. Antibiotics, vol. 28, pp. 358-365, (1975).
Takasawa, S., et al., J. Antibiotics, vol. 28, pp. 366-371, (1975).
Kawaguchi, H., et al., J. Antibiotics, vol. 30, pp. 779-788, (1977).

Primary Examiner—Delbert R. Phillips
Assistant Examiner—Blondel Hazel
Attorney, Agent, or Firm—Schuyler, Banner, Birch, McKie & Beckett

[57] ABSTRACT

N-methylbleomycins represented by the general formula

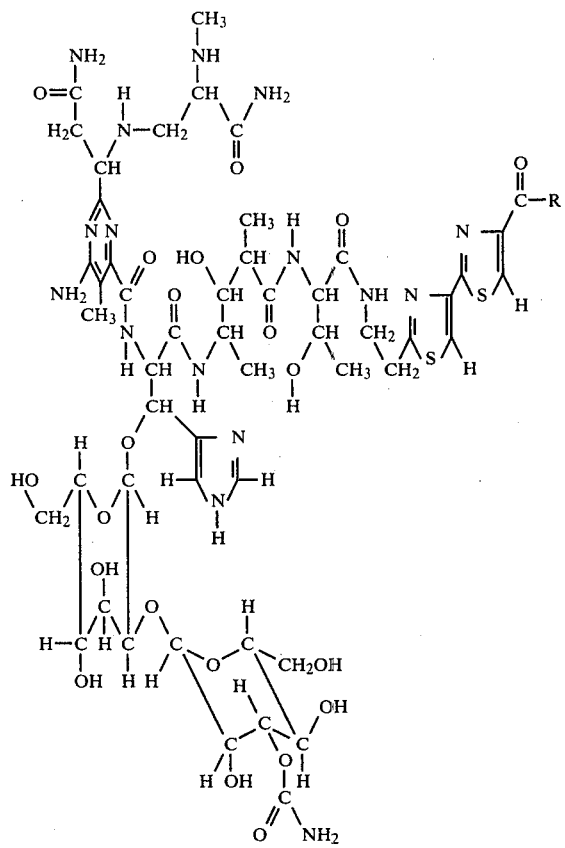

which are useful as antitumor agents and bactericides; a method of preparing the same; and intermediate products in the preparation thereof.

8 Claims, 14 Drawing Figures

BLEOMYCIN GROUP ANTIBIOTICS

BACKGROUND OF THE INVENTION

This invention relates to new bleomycin group antibiotics.

Bleomycins are antitumor antibiotics discovered by Umezawa et al., which are produced by an Actinomycete, *Streptomyces verticillus* [Umezawa et al., Journal of Antibiotics, 19A, p. 200 (1966)], and have structures represented by the formula [I]

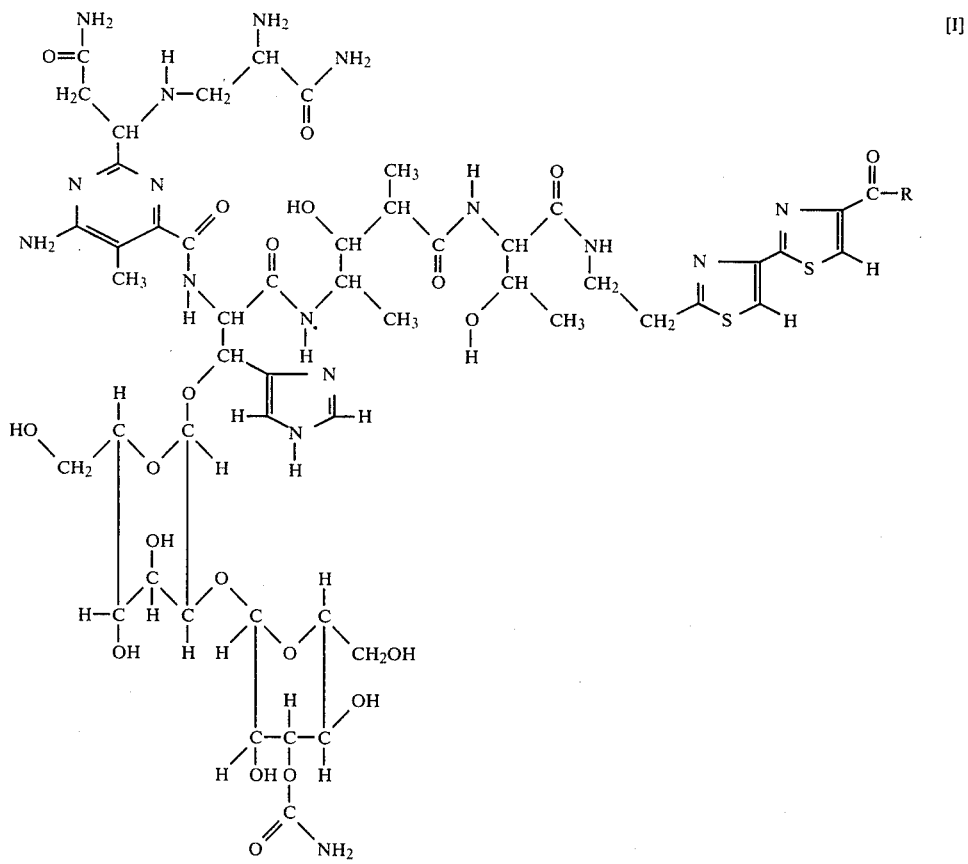

wherein R represents a terminal amine moiety of bleomycins.

A mixture comprising bleomycins $A_2$ and $B_2$ as major constituents is currently exhibiting an excellent effect in the chemotherapy of cancers, chiefly squamous cell carcinomas, particularly in the field of head and neck cancer, skin cancer, penis cancer, uterine cervix cancer, esophageal cancer, lung cancer, and malignant lymphoma.

When subjected to the action of an inactivating enzyme, however, conventional bleomycins are inactivated through the hydrolysis of a portion of their structure represented by the partial structural formula

as shown by the following scheme:

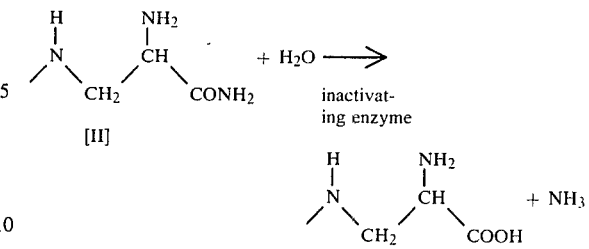

This fact was demonstrated by employing animal organs such as mouse liver. It was also found that bleomycins are comparatively resistant to inactivation in skin and lung where they act very actively, whereas easily subjected to inactivation in stomach and other organs where they do not act. It was further found that the inactivation action is weaker in the squamous cell carcinoma in mice than in the sarcoma in mice, both of which are induced by 20-methylcholanthrene [Umezawa et al., Journal of Antibiotics, 25, p. 409 (1972); Umezawa et al., Journal of Antibiotics, 27 p. 419 (1974)].

Moreover, it was found that the bleomycin-inactivating action is shown by squamous cell carcinoma in human head and neck resions, particularly markedly by those of the low differentiation type which are reported to be treated relatively ineffectively by bleomicins [Mueller et al., Cancer, 40, p. 2787 (1977)]. This is one of the reasons for the required improvement in bleomycins.

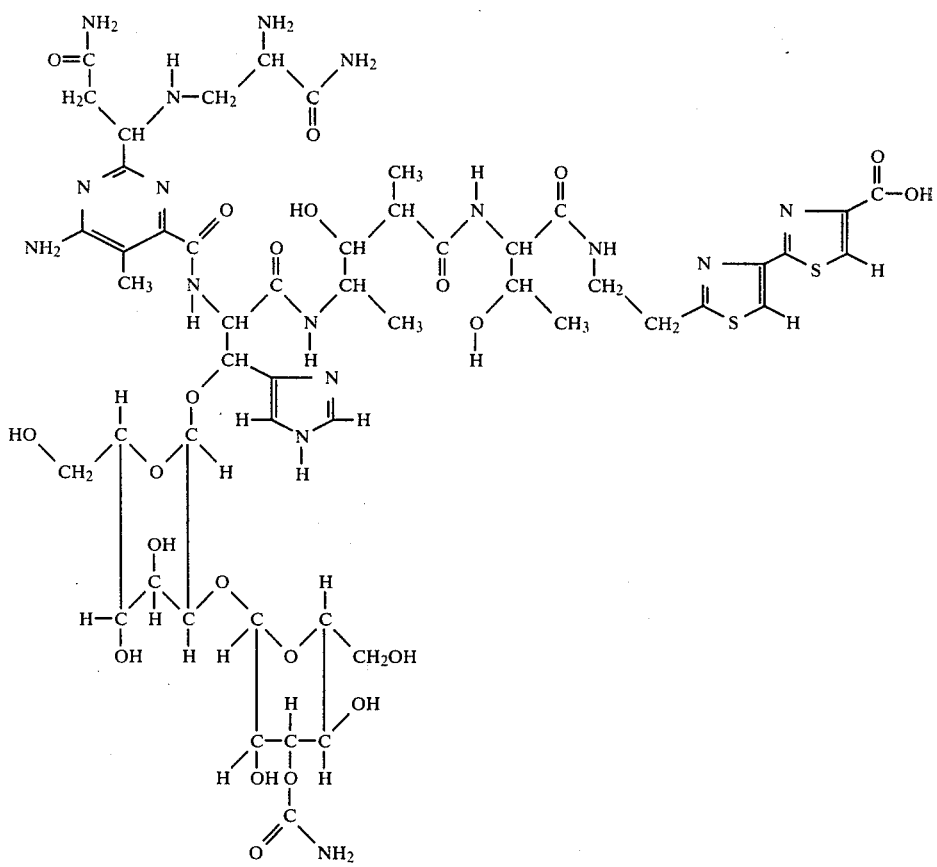

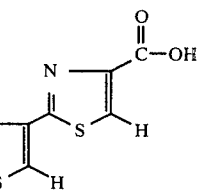

is subjected to reductive methylation, thus methylating the amine group

in the partial structural formula

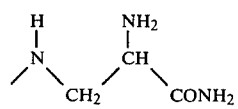

to convert [II] into the partial structural formula

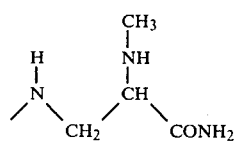

and the resulting methylated product is allowed to react with an amine in a customary manner of peptide linkage formation to obtain a N-methylbleomycin of the formula [IV], or a copper-chelated complex thereof or a non-toxic salt thereof.

The N-methylbleomycin group antibiotics of this invention are useful as antitumor agents or bactericides.

The terms "bleomycins", "bleomycinic acid", "N-methylbleomycins", and "N-methylbleomycinic acid" as used herein include both copper-free and copper-chelated forms, unless specifically indicated as copper-free form or copper-chelated form.

BRIEF DESCRIPTION OF THE DRAWINGS

In the accompanying drawings,

FIG. 1-(1) shows the residual activity of N-methylbleomycin $A_2$;

FIG. 1-(2) that of bleomycin $A_2$;

FIG. 2-(1) that of N-methylbleomycin $B_2$;

FIG. 2-(2) that of bleomycin $B_2$;

FIG. 3-(1) that of 3-[(S)-1'-phenylethylamino]-propylamino-N-methylbleomycin;

FIG. 3-(2) that of 3-[(S)-1'-phenylethylamino]-propylaminobleomycin;

FIG. 4-(1) that of 3-(3-n-butylaminopropylamino)-propylamino-N-methylbleomycin;

FIG. 4-(2) that of 3-(3-n-butylaminopropylamino)-propylaminobleomycin;

FIG. 5-(1) that of N-methylbleomycin $A_2'$-b;

FIG. 5-(2) that of bleomycin $A_2'$-b;

FIG. 6-(1) that of N-methylbleomycinic acid; and

FIG. 6-(2) that of bleomycinic acid.

FIG. 7 being that of N-methylbleomycinic acid (copper-chelated form),

FIG. 8 that of N-methylbleomycin $A_2$ (copper-chelated form) hydrochloride,

FIG. 9 that of N-methylbleomycin $A_2$ (copper-free form) hydrochloride, and

FIG. 10 that of N-methylbleomycin $B_2$ (copper-free form) hydrochloride.

DETAILED DESCRIPTION OF THE INVENTION

Figure 1:
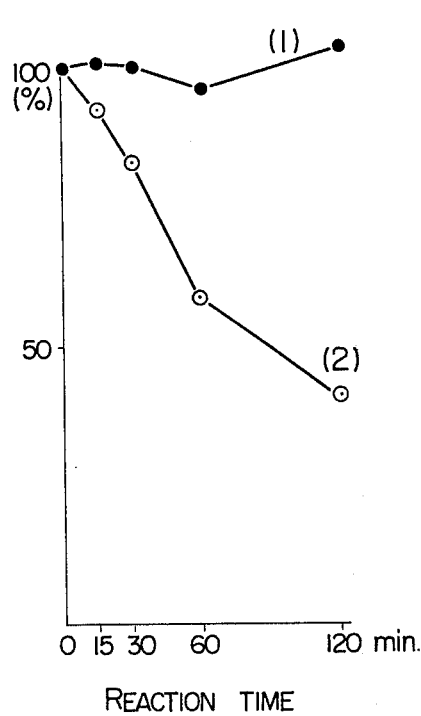
FIGS. 1 to 6 show the residual activities of the present compounds and corresponding conventional bleomycins against an inactivating enzyme, the ordinate representing the residual activity (%) and the abscissa the reaction time.
Figure 2:
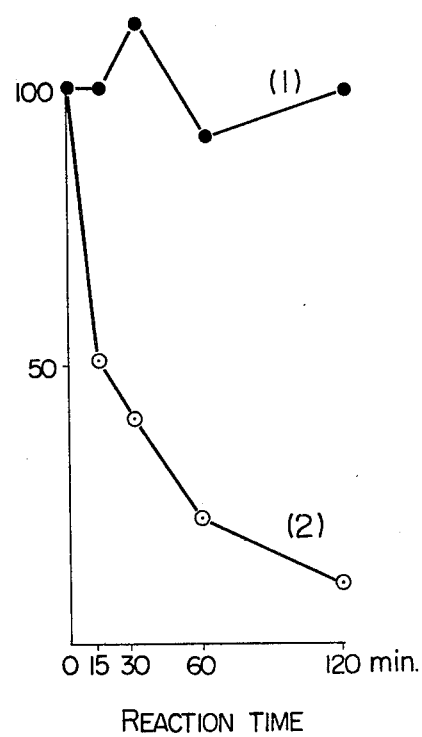
Figure 3:
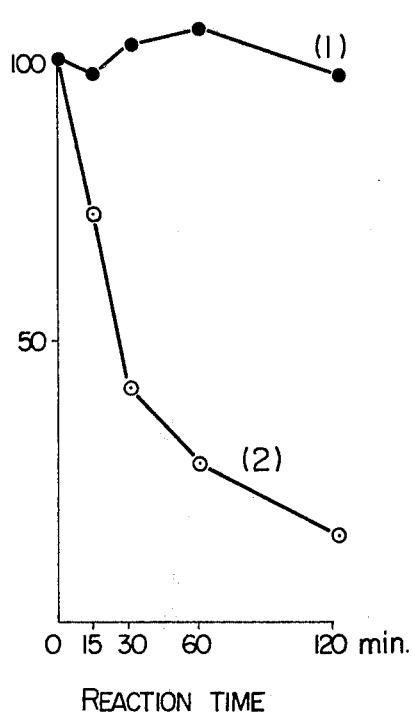
Figure 4:
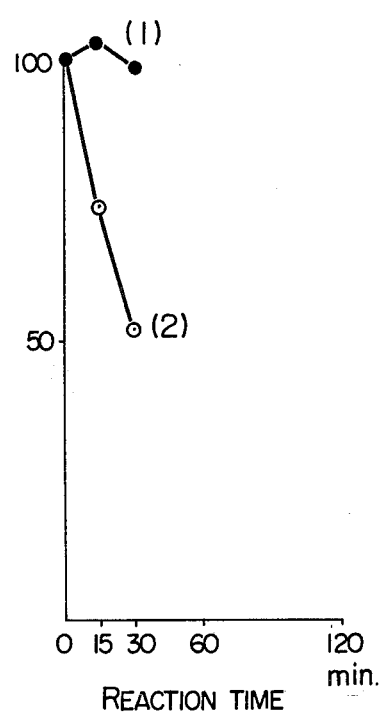
Figure 5:
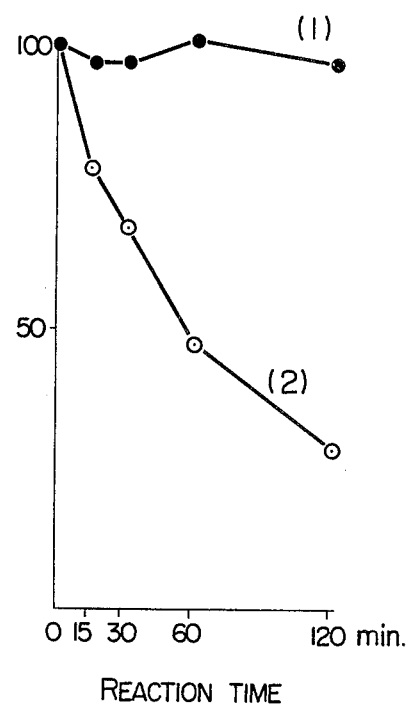
Figure 6:
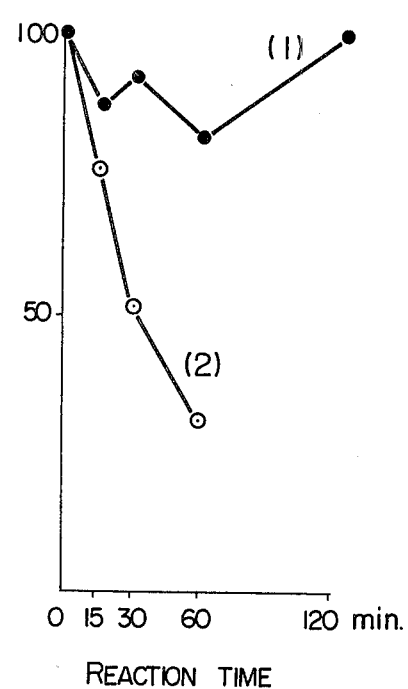

The method for producing compounds of this invention is explained below in more detail.

First method: The bleomycin group antibiotics used as starting materials in preparing the present N-methylbleomycin group antibiotics of the general formula [IV] by the first method include bleomycins obtained from the cultivation broth of Streptomyces verticillus by the well-known procedure [Umezawa et al., Journal of Antibiotics, 19, p. 210 (1966)], bleomycins produced by the method in which an amino compound is added as precursor in cultivation (U.S. Pat. No. 3,846,400), bleomycins described in DT-OS No. 2,828,933, N-substitution derivatives in the terminal amine groups of bleomycins (U.S. Pat. No. 3,922,262), zorbamycins B and C produced by Streptomyces bikiniensis var. zorbonensis [Argoudelis et al., Journal of Antibiotics, 24, p. 543 (1971)], victomycin produced by Streptosporangium violaceochromogenes [Kawamoto et al., Journal of Antibiotics, 28, p. 358 (1975)], platomycins A and B produced by Streptosporangium violaceochromogenes sub sp. globophilum [Takasawa et al., Journal of Antibiotics, 28, p. 366 (1975)], and tallysomycins A and B produced by No. E465-94 strain belonging to Actinomycetes [Kawaguchi et al., Journal of Antibiotics, 30, p. 779 (1977)].

The reductive methylation of bleomycin group antibiotics is carried out by reacting formaldehyde with said antibiotics in the presence of a reducing agent preferably in an inert solvent which dissolves said antibiotics. The reducing agents used in the reductive methylation include sodium borohydride compounds such as sodium cyanoborohydride and derivatives of formic acid. The reductive methylation can be effected by catalytic reduction in the presence of a catalyst such as palladium-carbon. The amount of formaldehyde used in the reductive methylation is preferably 1.0 to 1.5 moles per mole of bleomycin group antibiotics. The reducing agent is used preferably in an amount of 0.6 to 2 moles per mole of bleomycin group antibiotics. The reaction temperature is 0° to 50° C., preferably about 15° C. to about 35° C.

When those bleomycin group antibiotics such as 3-aminopropylaminobleomycin {a compound of the general formula [IV] in which R is 3-aminopropylamino group} which have a free primary amine group except for aromatic primary amine group

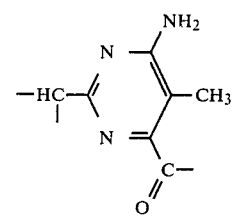

in addition to the partial structural formula [II] are used as starting materials, said free primary amine group is also methylated, resulting sometimes in a decrease in the yield of intended N-methyl derivative. In such a case, the intended N-methyl derivative is obtained in a high yield by first protecting the primary amino group in the partial structural formula [II] by chelating with copper or the like, introducing in a customary manner an amino-protecting group such as tert-butoxycarbonyl group into said free amine group, removing the metal agent, then subjecting the resulting compound to reductive methylation, and, after the reaction, removing the protective group by a suitable known method such as treatment with trifluoroacetic acid.

The inert solvents which dissolve bleomycin group antibiotics are suitably selected, depending upon particular type of bleomycins, from polar solvents such as, for example, water, methanol, dimethyl sulfoxide, and the like.

Second method: The preparation of N-methylbleomycin group antibiotics of the general formula [IV] by the second method is carried out in the following manner.

Bleomycinic acid is reductively methylated by reacting with formaldehyde in an inert solvent in the presence of a reducing agent, whereby

of the partial structural formula [II] is methylated and transformed into the partial structural formula [III], yielding N-methylbleomycinic acid represented by the general formula [VI],

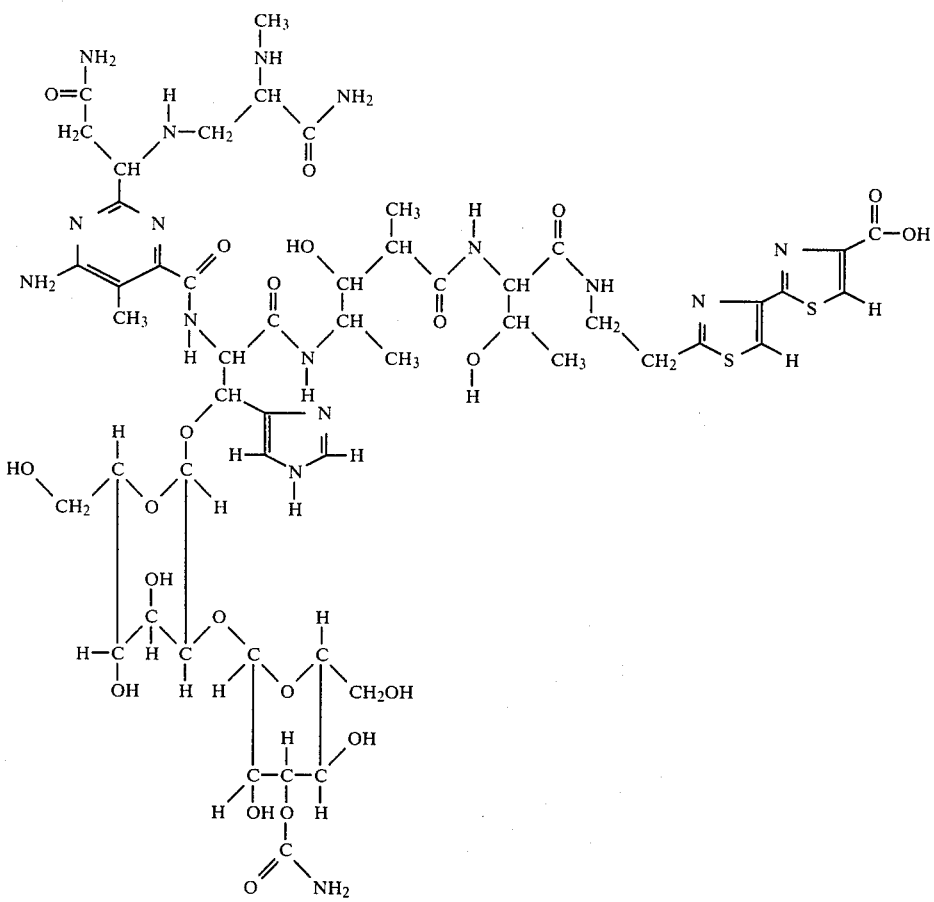

[VI]

This acid is then subjected to the customary peptide forming treatment by reacting with an amine of the general formula

R—H [VII]

(where R is the same as defined before) in the presence of a condensation reagent for peptide synthesis. Alternatively, N-methylbleomycinic acid of the general formula [VI] is converted into an active ester such as is used in usual peptide synthesis and then reacted with an amine of the general formula [VII].

The inert solvents used in the reductive methylation of the first step are preferably those which dissolve bleomycinic acid such as polar solvents including water, aqueous methanol, dimethylformamide, dimethyl sulfoxide, and the like. The reducing agents are the same as used in the first method, borohydride compounds such as sodium cyanoborohydride being preferred. The bleomycinic acid used as starting material is a known compound which is prepared, as described in U.S. Pat. No. 3,843,448, by exposing bleomycin $B_2$ to the action of cultivated cells of a strain of the Fusarium genus such as, for example, Fusarium roseum Link emend Synder et Hansen, ATCC 20352 or ATCC 20355, Fusarium anguioides Sherbakoff, ATCC 20351, or a strain of Helminthosporium genus such as Helminthosporium zonatum Ikata et Yoshida, ATCC 20353 or ATCC 20354. The amount of formaldehyde used in the reductive methylation is 0.5 to 5 moles, preferably 1.0 to 1.5 moles per mole of bleomycinic acid. The amount of sodium cyanoborohydride is 0.3 to 4 moles, preferably 0.6 to 2 moles per mole of bleomycinic acid. The temperature of the reductive methylation is 0° to 50° C., preferably 15° to 35° C.

When the reductive methylation has sufficiently proceeded, the excess reducing agent, if any, is decomposed to terminate the reaction. In case the reducing agent is sodium cyanoborohydride for example, the reaction is terminated by reducing pH below 3, preferably to about 1 with hydrochloric acid. Although in some cases the reaction solution can be used as such in the succeeding step of the reaction with an amine, it is usual practice to isolate N-methylbleomycinic acid from the reaction solution is effected, similarly to the isolation of known bleomycins, by use of a suitable adsorbent resin such as, for example, a non-ionexchangeable macroreticular resin or the like and through a sequence of adsorption, desalting and elution in the following manner.

The reaction solution is adjusted to pH about 6 with an alkali such as sodium hydroxide or the like, then freed from the solvent by distillation, and fed to a column filled with distilled water and an adsorbent resin such as, for example, Amberlite® XAD-2 (trademark for an adsorbent composed of styrene-divinylbenzene copolymer, manufactured by Rohm & Haas Co.) to adsorb the intended substance onto the resin for the purpose of desalting. After washing with distilled water to remove the salts, the adsorbed substance is eluted with an acidic aqueous methanol such as, for example, a N/50 hydrochloric acid-methanol (1:4 V/V) mixture to collect a fraction which show an absorption maximum at a wave-length of about 290 mμ. The fraction is neutralized with an anion-exchange resin Dowex 44® [OH⁻ type; a weekly basic anion-exchange resin compound of a condensation product between epichlorohydrin and ammonia (Dow Chemical Co.)], then concentrated in vacuo, and lyophilized to obtain a crude powder of N-methylbleomycinic acid. If required, the purity can be further improved in the following manner.

The powder obtained above is dissolved in distilled water and admixed with basic cupric carbonate under stirring, whereby the N-methylbleomycinic acid is transformed into a copper-complex. The complex is adsorbed onto a column packed with CM-Sephadex C-25® [Na⁺ type; an acidic ion-exchanger composed of carboxymethyl ether derivative of a dextran gel (Pharmacia Fine Chemicals, Inc.)] which has been equilibrated with a 1/20 M-acetic acid-sodium acetate buffer solution of pH 4.5. The adsorbed phase is eluted by the linear gradient method by using as eluent the said buffer solution to which is added continuously sodium chloride to increase gradually the sodium chloride concentration up to 1.0 M. The N-methylbleomycinic acid is eluted at a sodium chloride concentration of about 0.35 M. Since both the unreacted starting material and the impurities are eluted at an earlier stage, the fractions containing these substances can be removed by detecting with an ultraviolet absorption monitor such as, for example, Uvicord® (LKB Co.). If the intended fraction is found to be contaminated with impurities, the latter can be entirely removed by repeating the above chromatography. The intended fraction thus obtained is desalted by the above-mentioned method which employs Amberlite XAD-2 and is then lyophilized to obtain N-methylbleomycinic acid copper complex in the form of amorphous powder, bluish purple in color.

The step (second step) of converting the above intermediate product into a N-methylbleomycin is described below. This step is characterized by activating the carboxyl group with a condensation reagent for peptide synthesis and then reacting the activated intermediate with an amine of the general formula [VII] to obtain a N-methylbleomycin. The procedure is described below in detail by referring to an example.

N-methylbleomycinic acid is dissolved in water, an organic solvent, or a mixture thereof. Preferred organic solvents are dimethylformamide and dimethyl sulfoxide. Into the solvent, are added with stirring at a certain temperature between 0° and 50° C., preferably between 0° and 30° C., a basic catalyst such as, for example, N-methylmorpholine and a condensation reagent for piptide synthesis such as, for example, 6-chloro-1-p-chlorobenzenesulfonyloxybenzotriazole (hereinafter referred to as CCBT). Thereafter, an amine of the general formula [VII] is added and allowed to react for 0.5 to 24 hours, preferably 1 to 5 hours and, if necessary, the reaction is terminated by adding acetic acid to obtain a reaction solution containing a N-methylbleomycin. When the starting material is copper-free or a copper complex, there is obtained a N-methylbleomycin in copper-free form or copper-complex form, respectively. In isolating the product in the succeeding step, the copper-complex form is preferred. Both the condensation reagent for peptide synthesis and the amine of the general formula [VII] are used in an amount of 0.5 to 10, preferably 1 to 5 moles for 1 mole of N-methylbleomycinic acid.

Examples of amines of the general formula [VII] include those in which —R is of the formula

wherein $Y_1$ is an

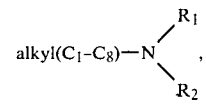

where $R_1$ and $R_2$ are each (a) an alkyl($C_1$–$C_8$) which may be substituted by a hydroxyl or an alkoxy($C_1$–$C_8$), (b) a phenylalkyl($C_1$–$C_2$) which may be substituted by a methyl,

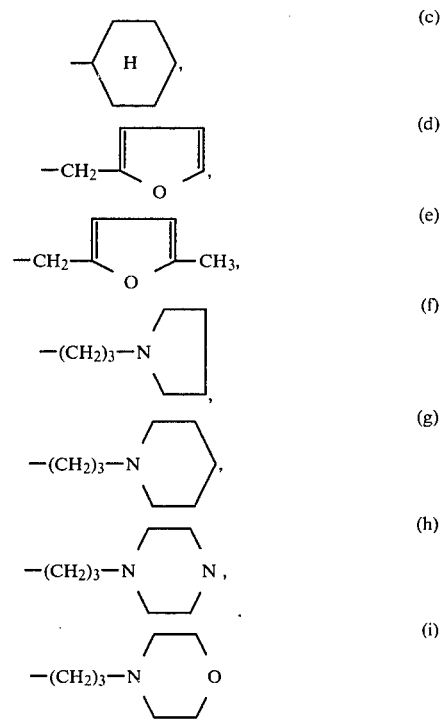

or (j) a hydrogen atom; an

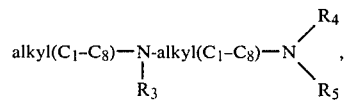

where $R_3$ is a hydrogen atom or an alkyl($C_1$–$C_8$) and $R_4$ and $R_5$ are a hydrogen atom, an alkyl($C_1$–$C_4$) or a benzyl; an alkyl($C_1$–$C_5$)-NH-alkyl($C_1$–$C_6$)-alkyl($C_1$–$C_5$)-$NH_2$;

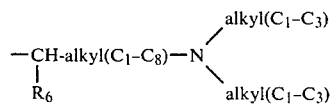

wherein $R_6$ is —COOH or —$CONH_2$; a phenyl which may be substituted by an alkyl($C_1$–$C_3$), —$NO_2$, —CN, —$SO_3H$,

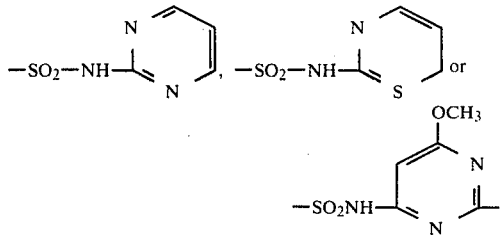

phenylalkyl($C_1$-$C_3$) which may be substituted on the phenyl ring by an aminomethyl; an alkyl($C_1$-$C_4$)-$R_7$, wherein $R_7$ is

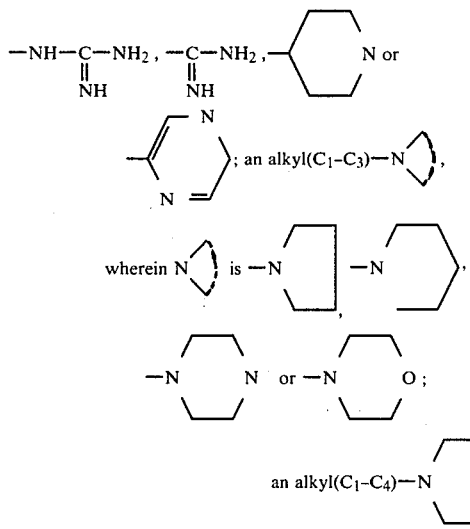

wherein $R_8$ is an alkyl($C_1$-$C_3$), or an aminoalkyl($C_1$-$C_4$); an

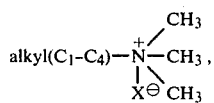

wherein X is a chlorine or a bromine atom;

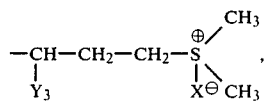

where $Y_3$ is a hydrogen atom, —COOH or —$CONH_2$ and X is as defined above; biphenyl; naphthyl or pyridyl, and $Y_2$ is a hydrogen atom, —$CH_3$, —$COCH_3$, —$COC_2H_5$ or

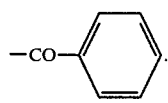

Examples of individual amines include hydroxylamine, hydrazine, phenylhydrazine, semicarbazide, thiosemicarbazide, dicyclohexylcarbodiimide, methylamine, ethylamine, n-propylamine, isopropylamine, n-hexylamine, n-laurylamine, allylamine, dimethylamine, dipropylamine, cyclohexylamine, cyclopentylamine, aniline, aminopyridine, aminopyrimidine, aminothiazole, aminoimidazole, aminopyrazole, aminotriazole, naphthylamine, aminoquinoline, ethyleneimine, pyrolidine, piperidine, and morpholine. Examples of substituted amines include cyanomethylamine, β-hydroxyethylamine, β-cyanoethylamine, β-bromoethylamine, 1,3-trimethylenediamine, 1,4-diaminobutane, 4-guanidinobutylamine, di-β-chloroethylamine, amino acid esters (for example, glycine methyl ester, phenylglycine methyl ester, phenylalanine methyl ester, lysine methyl ester, etc.), cyclohexylmethylamine, chloroaniline, nitroaniline, anisidine, toluidine, cyanoaniline, aminoacetophenone, aminoacetanilide, biphenylamine, benzylamine, phenethylamine, sulfanilic acid, sulfanylamide, sulfadiazine, sulfathiazole, sulfadimethoxine, homosulfamine, furfurylamine, 4-(5-nitro-2-furyl)-thiazolylamine, 1,2-diaminoethane, 1,3-diaminopropane, 1,4-diaminobutane, 1,5-diaminopentane, 1,6-diaminohexane, N-(2-aminoethyl)-1,2-diaminoethane, N-(3-aminopropyl)-1,3-diaminopropane, N-(3-aminopropyl)-1,4-diaminobutane, N-(3-aminopropyl)-1,6-diaminohexane, N-(5-aminopentyl)-1,5-diaminopentane, N,N'-bis(2-aminoethyl)diaminomethane, N,N'-bis(2-aminoethyl)-1,2-diaminoethane, N,N'-bis(3-aminopropyl)-1,4-diaminobutane, N,N'-bis(3-aminopropyl)-1,6-diaminohexane, N,N'-bis(5-aminopentyl)-1,5-diaminopentane, 2,2,3-trimethylpentamethylenediamine, 1,2-diaminopropane, N-methyl-1,3-diaminopropane, N-butyl-1,3-diaminopropane, N,N-dimethyl-1,2-diaminoethane, N,N-diethyl-1,2-diaminoethane, N,N-dimethyl-1,3-diaminopropane, N,N-diethyl-1,3-diaminopropane, 3-aminopropyl-trimethylammonium bromide, N-(3-dimethylaminopropyl)-1,3-diaminopropane, N-(3-methylaminopropyl)-1,2-diaminoethane, N-(3-methylaminopropyl)-1,4-diaminobutane, N-(3-methylaminopropyl)-1,5-diaminohexane, N-(3-methylaminopropyl)-1,8-diaminooctane, N-butyl-N'-3-aminopropyl-1,3-diaminopropane, N-(2-dimethylaminoethyl)-1,3-diaminopropane, N-(4-dimethylaminobutyl)-1,3-diaminopropane, N-(6-dimethylaminohexyl)-1,3-diaminopropane, N-(8-dimethylaminooctyl)-1,3-diaminopropane, N-(3-hydroxypropyl)-1,3-diaminopropane, N-(2-hydroxypropyl)-1,2-diaminoethane, N-(2-hydroxyethyl)-1,3-diaminopropane, N-(3-methoxypropyl)-1,3-diaminopropane, N-(3-octyloxypropyl)-1,3-diaminopropane, N-(3-amino-1-methylpropyl)-1,3-diaminopropane, N-(3-amino-1-ethylpropyl)-1,3-diaminopropane, N,N-bis(3-aminopropyl)methylamine, N,N-bis(3-aminopropyl)ethylamine, N,N-bis(3-aminopropyl)-n-butylamine, 3-aminopropyldimethylsulfonium bromide, 3-aminopropyldimethylsulfonium chloride, 3-acetamidopropyldimethylsulfonium bromide, 3-amino-3-carboxypropyldimethylsulfonium chloride, 3-amino-3-carbamoylpropyldimethylsulfonium chloride, 4-(aminobutyl)guanidine, 3-amidinopropylamine, N-(3-aminoproyl)pyrrolidine, N-(3-aminopropyl)piperidine, N-(2-aminoethyl)piperazine, N-(3-aminopropyl)piperazine, N-(3-aminopropyl)-morpholine, N-(3-aminopropyl)-N'-methylpiperazine, N-(3-aminopropyl)-N'-ethylpiperazine, N,N'-bis(3-aminopropyl)piperazine, N-(3-pyrrolidinopropyl)-1,3-diaminopropane, N-(3-piperidinopropyl)-1,3-diaminopropane, N-(3-morpholinopropyl)-1,3-diaminopropane, N-benzyl-1,3-diaminopropane, N,N-dibenzyl-1,3-diaminopropane, N-(1-phenylethyl)-1,3-diaminopropane, N-(p-methylbenzyl)-1,3-diaminopropane, m- xylenediamine, p-xylenediamine, N-cyclohexyl-1,3-diaminopropane, N-(3-cyclohexylaminopropyl)-1,3-diaminopropane, N-(2-hydroxycyclohexyl)-1,3-diaminopropane, N-(2-phenylethyl)-1,3-diaminopropane, N-(2-p-tolylethyl)-1,3-diaminopropane, N-benzyl-N'-(3-aminopropyl)-1,3-diaminopropane, N-(1-phenylethyl)-N'-(3-aminopropyl)-1,3-diaminopropane, N-(2-furfuryl)-1,3-diaminopropane, N-(5-methyl-2-furfuryl)-1,3-diaminopropane, N,N-dimethyl-1,3-diaminopropane, 4-piperidylmethylamine, 2-(4-imidazolyl)ethylamine, N,N-dimethyl-N'-acetyl-1,3-diaminopropane, N,N-dimethyl-N'-propionyl-1,3-diaminopropane, 1-carboxy-4-dimethylaminobutylamine, 1-carbamoyl-4-dimethylaminobutylamine, N,N-dimethyl-N'-benzoyl-1,3-diaminopropane, N-[2-($\beta$-pyridyl)ethyl]-1,3-diaminopropane, N-(2-methoxyethyl)-1,3-diaminopropane, and N-(1-methyl-3-methoxypropyl)-1,3-diaminopropane.

The condensation reagents for peptide synthesis for use in the second step reaction include N-ethyl-5-phenylisoxazolium-3'-sulfonate (NEPIS), N-tert-butyl-5-methylisoxazolium perchlorate, N-ethoxycarbonyl-2-ethoxy-1,2-dihydroquinoline, di-p-nitrophenyl sulfite ester, dicyclohexylcarbodiimide (DCC), 1-ethyl-3-(3-dimethylaminopropyl)carbodiimide, and 1-cyclohexyl-3-(2-morpholinoethyl)carbodiimide in addition to the aforementioned CCBT.

The isolation of N-methylbleomycin group antibiotics from the reaction solution obtained by the first or second method is effected by adsorption to a suitable adsorbent resin, followed by desalting and subsequent elution in a manner similar to that which is customary in isolating bleomycins. More detailed description of the procedure is given below.

The reaction solution is adjusted to pH 6.0 with sodium hydroxide, then freed from the methanol by distillation under reduced pressure, and charged to a column packed with an adsorbent resin such as, for example, Amberlite ® XAD-2 (Rohm and Haas Co.) together with distilled water to adsorb the intended substance onto the resin for the purpose of desalting. After washing off the salts with distilled water, the adsorbed substance is eluted with an acidic aqueous methanol, e.g. a N/50-hydrochloric acid-methanol (1:4 V/V) mixture, and the fraction having an absorption maximum at a wave-length of around 290 m$\mu$ is collected. The fraction is neutralized with an anion-exchange resin such as, for example, Dowex ® 44 (OH⁻ type; Dow Chemical Co.), then concentrated under reduced pressure, and lyophilized to yield a crude powder of N-methylbleomycin group antibiotics. Further purification of the crude powder can be effected in a manner as described below.

The crude powder is dissolved in distilled water and admixed with a cupric salt such as basic cupric carbonate with stirring to form a copper complex of N-methylbleomycin group antibiotics. The copper complex is adsorbed onto a column packed with CM-Sephadex ® C-25 (Na⁺ type; Pharmacia Fine Chemicals, Inc.) which has been equilibrated with a M/20-acetic acid-sodium acetate buffer solution of pH 4.5. The adsorbed phase is eluted by the linear gradient method by using as eluent the said buffer solution to which is added continuously sodium chloride to increase gradually the sodium chloride concentration up to 1.0 M. The copper complex of N-methylbleomycin group antibiotics is eluted in a band between 0.50 M and 0.80 M according to its basicity. Since the unreacted starting material and by-products are eluted at an earlier stage, the fractions containing these substances can be removed by detecting with an ultraviolet absorption monitor such as, for example, Uvicord ® (LKB Co.). If the intended fraction is found to be contaminated with impurities, the latter can be completely removed by repeating the above chromatography. The fraction containing the copper-chelated N-methylbleomycin is desalting by the above-said method which employs Amberlite XAD-2 to obtain purified N-methylbleomycin copper complex. The intended N-methylbleomycin is obtained by removing copper from the copper complex by a known method such as, for example, a method described in U.S. Pat. No. 3,929,993 which employs EDTA. The procedure is described below by referring to an example.

The copper complex is dissolved in distilled water and charged to a column packed with Amberlite ® XAD-2 together with distilled water to adsorb the copper complex onto the resin. The column is washed with an aqueous solution containing 2% of sodium chloride and 5% of ethylenediaminetetraacetic acid disodium (hereinafter referred to as EDTA.Na$_2$) and the excess EDTA.Na$_2$ is removed with a 2% aqueous sodium chloride solution. After washing with distilled water, the column was eluted with an acidic aqueous methanol, e.g. a N/50 hydrochloric acid-methanol (1:4 V/V) mixture, to collect the fraction having an absorption maximum at wavelengths around 290 m$\mu$. The effluent is adjusted to pH 6.0 with Dowex ® 44 (OH⁻ type), then concentrated under reduced pressure, and lyophilized to obtain a powder of a N-methylbleomycin hydrochloride. When, for example, an aqueous sulfuric acid is used in place of the hydrochloric acid, the intended product is obtained in the form of sulfate. Thus, by selecting the type of acid used in the elutiion step, it is possible to obtain a non-toxic salt with any pharmacologically acceptable acid.

The $^{13}$C NMR spectra (determined by the proton noise decoupling method in heavy water) of the N-methylbleomycin group antibiotics isolated by the procedure described above showed the signal of methyl group introduced by the method of this invention corresponding to 32.7 ppm chemical shift. It was also confirmed that when a N-methylbleomycin is hydrolyzed in 6 N hydrochloric acid at 105° C. for 24 hours, 3-amino-2-methylaminopropionic acid and methylamine were found in the hydrolyzate. Other decomposition products common to bleomycins, except for 2,3-diaminopropane, were also detected in the hydrolyzate. The above facts indicate that the compounds prepared by the method of this invention have a partial structure represented by the partial structural formula [III].

Further, N-methylbleomycinic acid obtained as an intermediate product in the second method showed a $^{13}$C NHR spectrum (determined by the proton noise decoupling method in heavy water) in which the signal of the methyl group introduced by the method of this invention was detected at 32.7 ppm chemical shift. It was also confirmed that when N-methylbleomycinic acid is hydrolyzed in 6 N hydrochloric acid at 105° C. for 24 hours, 3-amino-2-methylaminopropionic acid and methylamine are found in the hydrolyzate. Accordingly, the N-methylbleomycinic acid prepared as an intermediate product in the second method has a partial structure represented by the partial structural formula [III].

Examples of N-methylbleomycins obtained according to this invention include the following compounds.

N-METHYLBLEOMYCINS

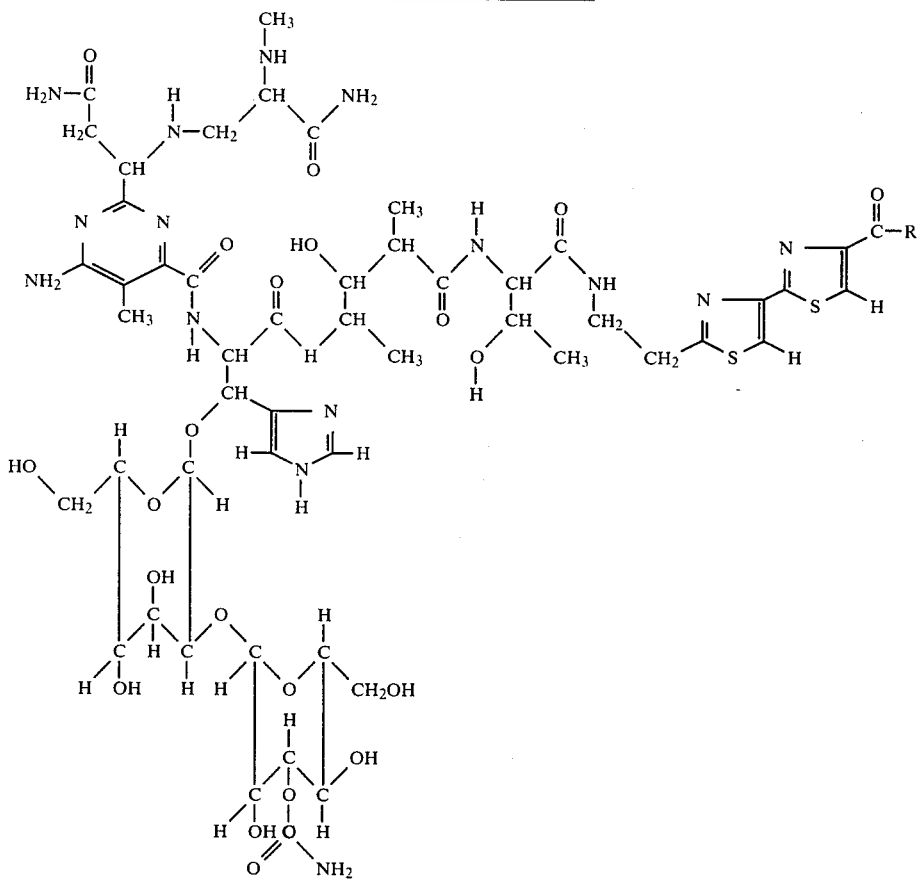

wherein R is:

wherein R is:
—NH—(CH$_2$)$_2$—NH$_2$
—NH—(CH$_2$)$_3$—NH$_2$

—NH—(CH$_2$)$_2$—N(CH$_3$)$_2$

—NH—(CH$_2$)$_2$—N(C$_2$H$_5$)$_2$

—NH—(CH$_2$)$_3$—N(CH$_3$)$_2$

—NH—(CH$_2$)$_3$—N(C$_2$H$_5$)$_2$

—NH—(CH$_2$)$_3$—NH—(CH$_2$)$_3$—N(C$_4$H$_9$)(H)

—NH—(CH$_2$)$_2$—NH—CH$_2$—CH(OH)—CH$_3$

-continued

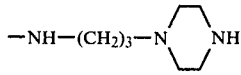

—NH—(CH$_2$)$_3$—NH—(CH$_2$)$_3$—NH—CH(CH$_3$)—C$_6$H$_5$

—NH—CH$_2$—CH(NH$_2$)—CH$_3$

—NH—(CH$_2$)$_3$—S$^{\oplus}$(CH$_3$)$_2$

—NH—(CH$_2$)$_4$—NH—C(=NH)—NH$_2$
—NH—(CH$_2$)$_3$—NH—CH$_3$
—NH—(CH$_2$)$_3$—NH—(CH$_2$)$_3$—CH$_3$
—NH—(CH$_2$)$_3$—NH—(CH$_2$)$_6$—NH$_2$

—NH—(CH$_2$)$_3$—N$^{\oplus}$(CH$_3$)$_3$

—NH—(CH$_2$)$_3$—NH—(CH$_2$)$_3$—N(CH$_3$)$_2$

—NH—(CH$_2$)$_3$—NH—(CH$_2$)$_3$—NH$_2$
—NH—(CH$_2$)$_3$—N(CH$_3$)—(CH$_2$)$_3$—NH$_2$

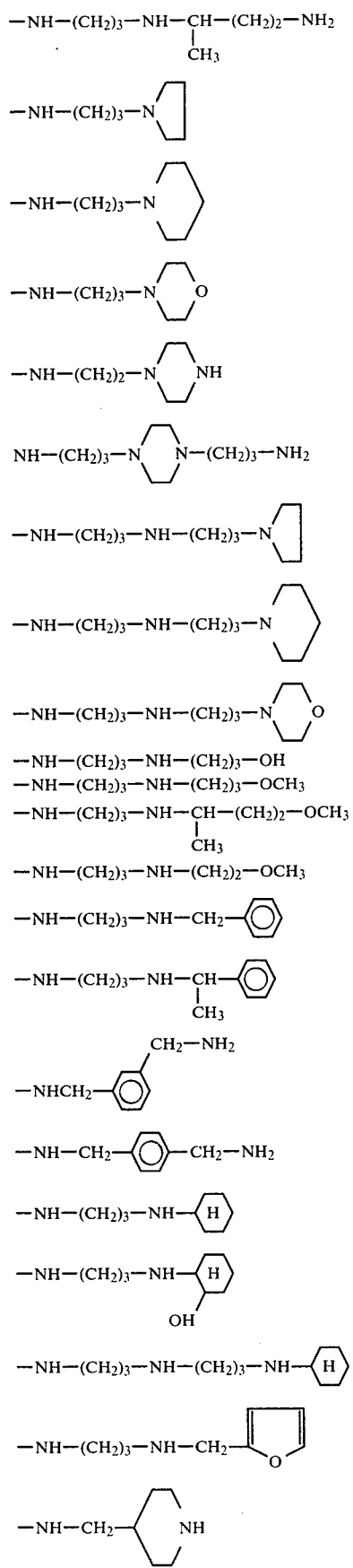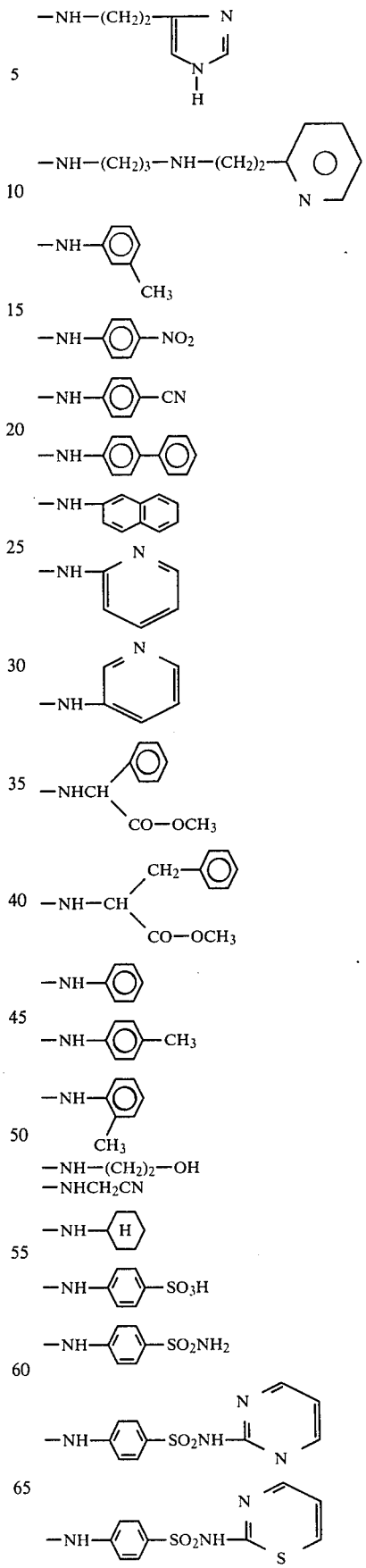

-continued

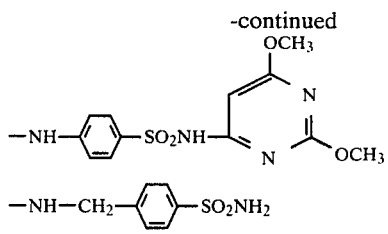

Main physical and chemical properties of N-methylbleomycinic acid and N-methylbleomycins determined on typical examples were as shown in Tables 1 to 3, wherein the compound numbers correspond to the following compounds.

Compound (1) N-methylbleomycinic acid
(2) N-methylbleomicin $A_2$

-continued

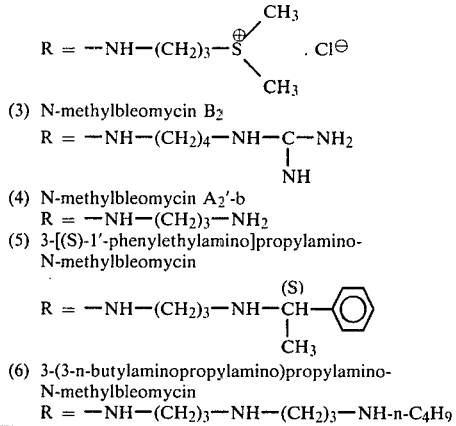

(3) N-methylbleomycin $B_2$
$R = -NH-(CH_2)_4-NH-\underset{\underset{NH}{\|}}{C}-NH_2$ (4) N-methylbleomycin $A_2'$-b
$R = -NH-(CH_2)_3-NH_2$ (5) 3-[(S)-1'-phenylethylamino]propylamino-N-methylbleomycin $$R = -NH-(CH_2)_3-NH-\overset{(S)}{\underset{\underset{CH_3}{|}}{CH}}-\text{C}_6\text{H}_5$$

(6) 3-(3-n-butylaminopropylamino)propylamino-N-methylbleomycin
$R = -NH-(CH_2)_3-NH-(CH_2)_3-NH$-n-$C_4H_9$

TABLE 1

| Physical and chemical property | Compound (1), Cu complex | Compound (2), Cu complex, hydrochloride | Compound (3), Cu complex, hydrochloride |
|---|---|---|---|
| Solubility | Soluble in water, DMF and DMSO | Soluble in water, DMF, DMSO and methanol | Same as in left column |
| Melting point, °C. (decomp.) | 218–220 | 206–208 | 199–201 |
| Molecular formula and molecular wt. | $C_{51}H_{72}N_{16}O_{22}S_2Cu$ 1388.89 | $C_{56}H_{85}N_{17}O_{21}S_3Cl_2Cu$ 1563.02 | $C_{56}H_{86}N_{20}O_{21}S_2Cl_2Cu$ 1573.99 |
| Circular dichroism, $[\theta]_\lambda^{25}$ (wavelength, m$\mu$) in distilled water | −4,900 (234) +9,100 (266) −6,700 (312) +2,800 (554) −1,400 (659) | −4,900 (234) +10,500 (270) −8,200 (313) +3,000 (558) −1,600 (663) | −2,700 (234) +9,900 (265) −8,000 (313) +2,900 (554) −1,500 (660) |
| TLC, Rf *1 | (a) 0.72 (b) 0.58 | (a) 0.38 (b) 0.49 | (a) 0.60 (b) 0.66 |
| Electrophoresis, Rm (Rm of alanine = *2 | 0.70 | 0.93 | 0.83 |

Note:
*1 (a) Silicagel 60F 254 ® (Merck Co.), methanol-10% ammonium acetate-10% aqueous ammonia (10:9:1 V/V)
   (b) Avicel S ® (FMC Co.), n-propanol-pyridine-acetic acid-water (15:10:3:12 V/V)
*2 Avicel SF ®, formic acid-acetic acid-water (25:75:900 V/V), 800 V, 15 minutes.

TABLE 2

| Physical and chemical property | Compound (1), Cu-free | Compound (2), Cu-free, hydrochloride | Compound (3), Cu-free, hydrochloride |
|---|---|---|---|
| Solubility | Soluble in water, DMF, DMSO | Soluble in water, DMF, DMSO and methanol | Same as in left column |
| Melting point, °C. (decomp.) | 194–196 | 183–185 | 186–188 |
| Molecular formula and molecular wt. | $C_{51}H_{74}N_{16}O_{22}S_2$ 1327.36 | $C_{56}H_{87}N_{17}O_{21}S_3Cl_2$ 1501.49 | $C_{56}H_{88}N_{20}O_{21}S_2Cl_2$ 1512.46 |
| Circular dichroism, $[\theta]_\lambda^{25}$ (wavelength, m$\mu$) in distilled water | −4,100 (248) +5,600 (286) −1,100 (316) | −5,600 (250) +6,500 (286) −500 (321) | −5,800 (250) +6,500 (286) −500 (322) |
| TLC, $R_f$*1 | (a) 0.38 (b) 0.59 | (a) 0.36 (b) 0.38 | (a) 0.34 (b) 0.70 |
| Electrophoresis, Rm (Rm of alanine = 1) *2 | 0.82 | 1.04 | 1.01 |

Note:
*1, *2 See note to Table 1.

TABLE 3

| Physical and chemical property | Compound (4), Cu-free, hydrochloride | Compound (5), Cu-free, hydrochloride | Compound (6), Cu-free, hydrochloride |
|---|---|---|---|
| Solubility | Soluble in water, DMF, DMSO and methanol | Same as in left column | Same as in left column |
| Melting point, °C. (decomp.) | 179–182 | 189–191 | 185–187 |
| Molecular formula and | $C_{54}H_{84}N_{18}O_{21}S_2Cl_2$ | $C_{62}H_{92}N_{18}O_{21}S_2Cl_2$ | $C_{61}H_{100}N_{19}O_{21}S_2Cl_3$ |

TABLE 3-continued

| Physical and chemical property | Compound (4), Cu-free, hydrochloride | Compound (5), Cu-free, hydrochloride | Compound (6), Cu-free, hydrochloride |
|---|---|---|---|
| molecular wt. | 1456.39 | 1560.54 | 1606.05 |
| Circular dichroism, $[\theta]_\lambda^{25}$ (wavelength, m$\mu$) in distilled water | −5,500 (247) +6,100 (284) − 400 (320) | −6,700 (250) +6,100 (287) − 300 (320) | −5,900 (247) +6,500 (286) − 400 (319) |
| TLC, Rf *1 | (a) 0.28 (b) 0.62 | (a) 0.35 (b) 0.80 | (a) 0.09 (b) 0.73 |
| Electrophoresis, Rm (Rm of alanine = 1) *2 | 1.03 | 1.04 | 1.25 |

Note:
*1, *2 See note to Table 1.

The biological properties of N-methylbleomycinic acid, an intermediate product, and N-methylbleomycins prepared by the method of this invention, as determined on the samples of typical examples, are described below.

1. Test for resistance to inactivating enzyme.

(1) Extraction of inactivating enzyme.

The liver of female Donryu strain rat was ground in twice by weight of M/15 phosphate buffer of pH 7.2 to prepare a tissue emulsion. The emulsion was centrifuged at 105,000×G for 60 minutes and the supernatant was dialyzed with the above buffer. A high molecular fraction thus obtained was used as the extract solution of an inactivating enzyme.

(2) Examination of inactivating reaction.

To 1 ml of the above extract solution, was added 1 ml (containing 800 mcg of N-methylbeleomycinic acid or a N-methylbeleomycins) of the substrate solution. The resulting mixture was allowed to react at 37° C. for 15, 30, 60 and 120 minutes. A 0.3 ml portion of the reaction solution was freed from protein and tested for the residual activity against *Mycobacterium smegmatis* ATCC 607. Similar tests were performed on bleomycinic acid and bleomycins, both of which had not been N-methylated. The results were as shown in FIGS. 1 to 6. In the FIGS., (1) and (2) represent the results pertaining to the compounds of this invention and the reference compounds, respectively.

As is evident from FIGS. 1 to 6, conventional bleomycinic acid and blemomycins are markedly susceptible to the action of inactivating enzyme and are inactivated with time, whereas N-methylbleomycinic acid and N-methylbleomycins of this invention are markedly resistant.

2. DNA-strand cleaving activity in cell-free system.

The mechanism of carcinostatic action of bleomycins has been believed to involve the cleavage of DNA chain caused by the joint action of copper-free bleomycins, divalent iron and molecular oxygen. Similar activity of N-methylbleomycins were also confirmed.

Testing method:

A mixture of divalent iron and a copper-free N-methylbleomycin was dissolved together with DNA labelled with tritium in a M/10 phosphate buffer of pH 7.4 The resulting solution was allowed to react in the presence of oxygen at 37° C. for 5 minutes. To the reaction mixture, was added 25% trichloroacetic acid. The precipitate was removed by centrifugation and the supernatant (acid-soluble fraction) was assayed for radioactivity to obtain the percentage of acid-soluble DNA in acid. This percentage was utilized as an index of the degree of DNA-strand cleavage. Similar test was repeated on bleomycins $A_2$ and $B_2$ used as reference. The results obtained were as shown in Table 4.

3. Growth inhibitory effect on cultured HeLa cells.

HeLa $S_3$ cells were inoculated into a medium (MEM with the addition of 10% calf serum) in a plastic Petri dish. After two days from the inoculation, N-methylbleomycinic acid or a N-methylbleomycin was added to the dish and after cultivation for further three days, the number of cells was counted. The growth inhibition (%) was calculated by the following equation:

$$\text{Growth inhibition (\%)} = (1 - \frac{A - C}{B - C}) \times 100$$

where A is the final number of cells on the third day from the addition of the test sample, B the final number of cells in a control culture without the addition of the test sample, and C the number of cells at the time of addition of the test sample. The value of $ID_{50}$ (concentration for 50% inhibition) was calculated from the graph obtained by plotting the concentration of sample against the growth inhibition. A similar test was performed on bleomycinic acid and bleomycins used as control. The results obtained were as shown in Table 5.

4. Antimicrobial activity against *Mycobacterium smegmatis* ATCC 607.

Method:

The antibacterial activity was assayed by the cylinder agar plate method against the above bacterium by assuming the activity of standard copper-free bleomycin $A_2$ to be 1,000 mcg units/mg. The results were as shown in Table 6. As is apparent from the table, N-methylbleomycins also exhibit excellent antibacterial activity.

As is seen from the experimental results described above, N-methylbleomycinic acid and N-methylbleomycins are not inactivated by the inactivating enzyme. Further, N-methylbleomycins retain the DNA cleaving activity similar to that of bleomycins and exhibit a high growth inhibitory activity toward HeLa $S_3$ cells as well as a high antimicrobial activity. These facts suggest the usefulness of the present compounds as antitumor agents and bactericides.

TABLE 4

| | Acid-soluble DNA (%) Sample concentration (mcg/ml) | | |
|---|---|---|---|
| Compound (copper-free) | 6.25 | 12.5 | 25 |
| Compound of this invention: | | | |
| N-methylbleomycin $A_2$ | 64.6 | 90.7 | 99.9 |
| N-methylbleomycin $B_2$ | 87.6 | 95.5 | 102.1 |
| N-methylbleomycin $A_2'$-b | 61.7 | 94.1 | 99.4 |
| 3-[(S)-1'-phenylethyl- | 70.1 | 92.6 | 100.5 |

TABLE 4-continued

| Compound (copper-free) | Acid-soluble DNA (%) Sample concentration (mcg/ml) | | |
|---|---|---|---|
| | 6.25 | 12.5 | 25 |
| amino]propylamino-N-methylbleomycin | | | |
| 3-(3-n-butylamino-propylamino)propyl-amino-N-methylbleomycin | 59.5 | 94.0 | 100.4 |
| Control: | | | |
| Bleomycin A$_2$ | 78.6 | 90.8 | 100.9 |
| Bleomycin B$_2$ | 85.6 | 95.8 | 98.2 |

TABLE 5

50% growth inhibitory concentration (ID$_{50}$, mcg/ml) against cultured HeLa S$_3$ cells

| N-methyl derivative (Cu-free) | | Conventional bleomycin (Cu-free) corresponding to compound in left column | |
|---|---|---|---|
| N-methylbleomycinic acid | 4.8 | Bleomycinic acid | 18 |
| N-methylbleomycin A$_2$ | 0.81 | Bleomycin A$_2$ | 0.73 |
| N-methylbleomycin B$_2$ | 0.35 | Bleomycin B$_2$ | 0.80 |
| N-methylbleomycin A$_2$'-b | 0.58 | Bleomycin A$_2$-b | 1.5 |
| 3-[(S)-1'-phenyl-ethylamino]propyl-amino-N-methyl-bleomycin | 0.30 | 3-[(S)-1'-phenyl-ethylamino]propyl-aminobleomycin | 0.52 |
| 3-(3-n-butylamino-propylamino)-propylamino-N-metylbleomycin | 0.37 | 3(3-n-butylamino-propylamino)-propylaminobleomycin | 0.43 |

TABLE 6

| Compound | Antimicrobial activity, mcg units/mg | |
|---|---|---|
| | Cu-free | Cu-complex |
| N-methylbleomycinic acid | 59 | 64 |
| N-methylbleomycin A$_2$ | 513 | 423 |
| N-methylbleomycin B$_2$ | 1,766 | 1,755 |
| N-methylbleomycin A$_2$'-b | 595 | 625 |
| 3-[(S)-1'-phenylethyl-amino]propylamino-N-methylbleomycin | 4,333 | 4,266 |
| 3-(3-n-butylamino-propylamino)propyl-amino-N-methylbleo-mycin | 3,438 | 3,695 |

The invention is illustrated below in detail with reference to Examples, but the invention is not limited thereto.

EXAMPLE 1

Synthesis of N-methylbleomycinic acid (copper complex)

In 48 ml of 85% aqueous methanol, was dissolved 1.0 g of bleomycinic acid (copper-free). To the solution, while being stirred at 30° C., was added an aqueous solution containing 30 mg of formaldehyde, followed by 33 mg of sodium cyanoborohydride. After 12 hours of reaction, the reaction system was adjusted to pH 1.0 with 1 N hydrochloric acid to terminate the reaction after 10 minutes of standing. The reaction mixture was neutralized with 1 N sodium hydroxide solution, freed from the methanol by distillation under reduced pressure, and the residue was made up to 10 ml with distilled water. For the purpose of desalting, the resulting solution was fed to a column packed with 300 ml of Amberlite ® XAD-2 with distilled water. After washing with distilled water, the column was eluted with a N/50 hydrochloric acid-methanol (1:4 V/V) mixture, and a fraction having an absorption maximum at wavelengths around 290 mµ was collected. The fraction was neutralized with an anion-exchange resin Dowex ® 44 (OH$^-$ type), then concentrated under reduced pressure, and lyophilized.

The lyophilized product was dissolved in 10 ml of distilled water, admixed with 113 mg of basic cupric carbonate, and stirred at room temperature for 2 hours. The excess basic cupric carbonate was removed by filtration and the bluish purple filtrate was charged to a column packed with 200 ml of CM-Sephadex ® C-25 (Na$^+$ type) which had been equilibrated with M/20 acetic acid-sodium acetate buffer of pH 4.5 to absorb the intended product. The column was eluted by the linear gradient method by using as eluent 2 liters of the said buffer solution to which was added continuously sodium chloride to increase gradually the sodium chloride concentration up to 1.0 M. An effluent fraction, bluish purple in color, at a sodium chloride concentration of about 0.35 M was collected. In order to improve the purity, the above chromatography was repeated and then the intended fraction was desalted in the same manner as before by using Amberlite ® XAD-2. The fraction thus treated was adjusted to pH 6.0 with Dowex ® 44 (OH$^-$ type), and concentrated under reduced pressure and then lyophilized to obtain 250 mg (24% yield) of N-methylbleomycinic acid (copper complex) in the form of bluish purple amorphous powder.

Figure 7:
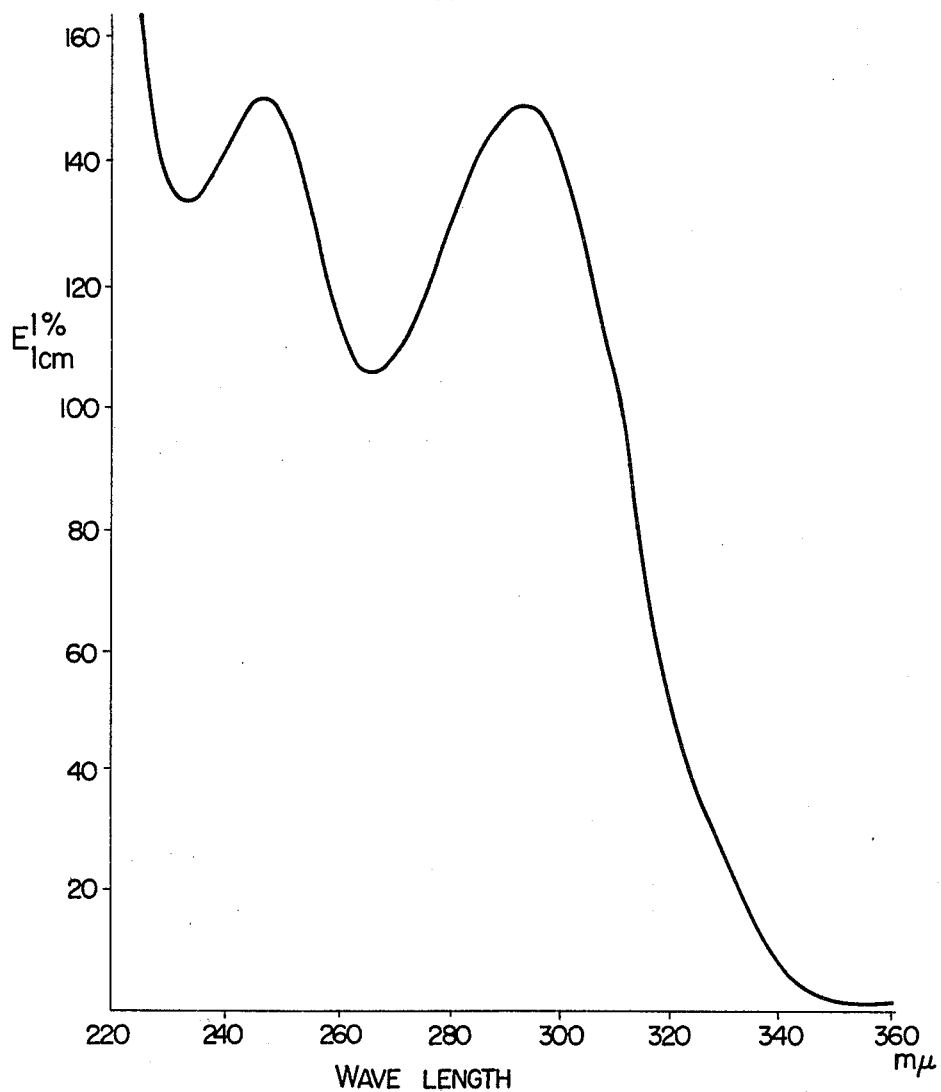
FIGS. 7 to 10 show ultraviolet absorption spectra of the present compounds.
Figure 11:
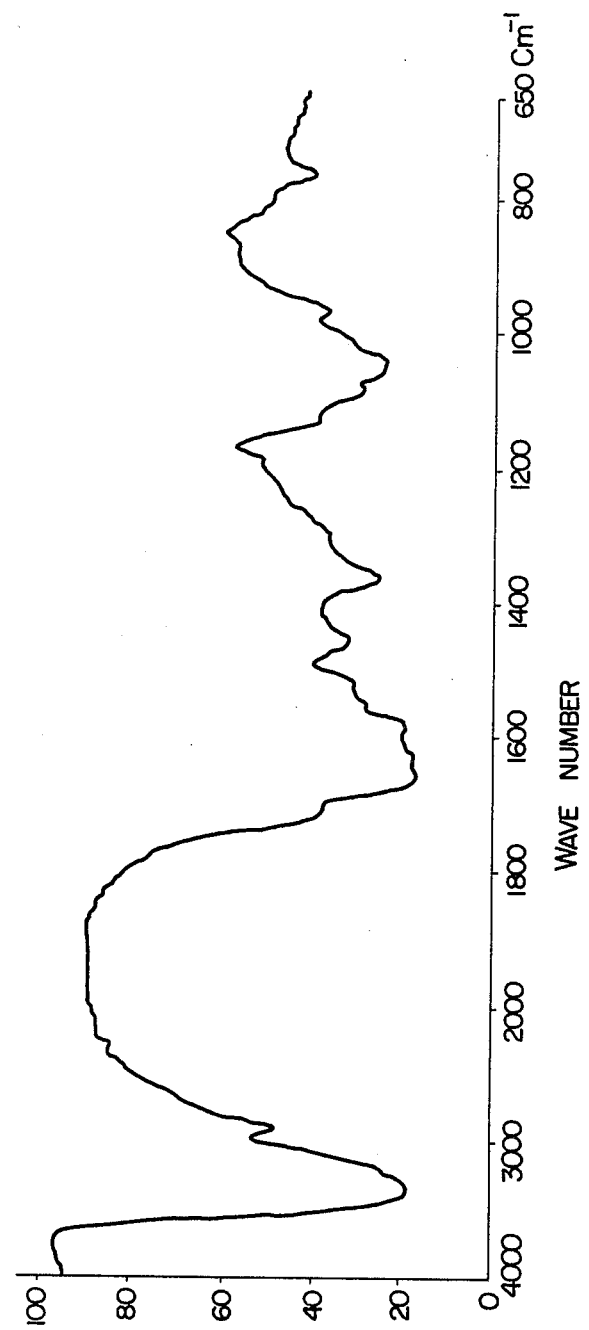
FIGS. 11 to 14 show infrared absorption spectra of the present compounds as determined by the potassium bromide tablet method, FIG. 11 being that of N-methylbleomycinic acid (copper-chelated form), FIG. 12 that of N-methylbleomycin $A_2$ (copper-chelated form) hydrochloride, FIG. 13 that of N-methylbleomycin $A_2$ (copper-free form) hydrochloride, and FIG. 14 that of N-methylbleomycin $B_2$ (copper-free form) hydrochloride.

The ultraviolet absorption spectrum of the powder, as measured in distilled water, and the infrared absorption spectrum taken by the potassium bromide tablet method, were as shown in FIGS. 7 and 11, respectively.

Ultraviolet absorption maxima (E$_{1cm}^{1\%}$, distilled water): 292 (150), 246 (151) mµ.

Other physical and chemical properties were as shown before in Table 1.

EXAMPLE 2

Synthesis of N-methylbleomycinic acid (copper complex)

In 50 ml of 90% aqueous methanol, was dissolved 1.0 g of bleomycinic acid (copper-free). To the solution, while being stirred at 0° C., was added an aqueous solution containing 34 mg of formaldehyde, followed by 72 mg of sodium cyanoborohydride. After 24 hours of reaction, the reaction solution was treated as in Example 1 to obtain 198 mg (19% yield) of N-methylbleomycinic acid (copper complex) in the form of bluish purple amorphous powder. This powder showed physical and chemical properties similar to those of the sample obtained in Example 1.

EXAMPLE 3

Synthesis of N-methylbleomycinic acid (copper complex)

In 40 ml of 95% aqueous methanol, was dissolved 1.0 g of bleomycinic acid (copper-free). To the solution, while being stirred at 23° C., was added an aqueous solution containing 25 mg of formaldehyde, followed by 62 mg of sodium cyanoborohydride. After 6 hours of reaction, the reaction mixture was treated as in Example 1 to obtain 235 mg (22% yield) of N-methylbleomycinic acid (copper complex) in the form of bluish purple amorphous powder. This powder showd physical and chemical properties similar to those of the sample obtained in Example 1.

EXAMPLE 4

Synthesis of N-methylbleomycin $A_2$

Figure 8:
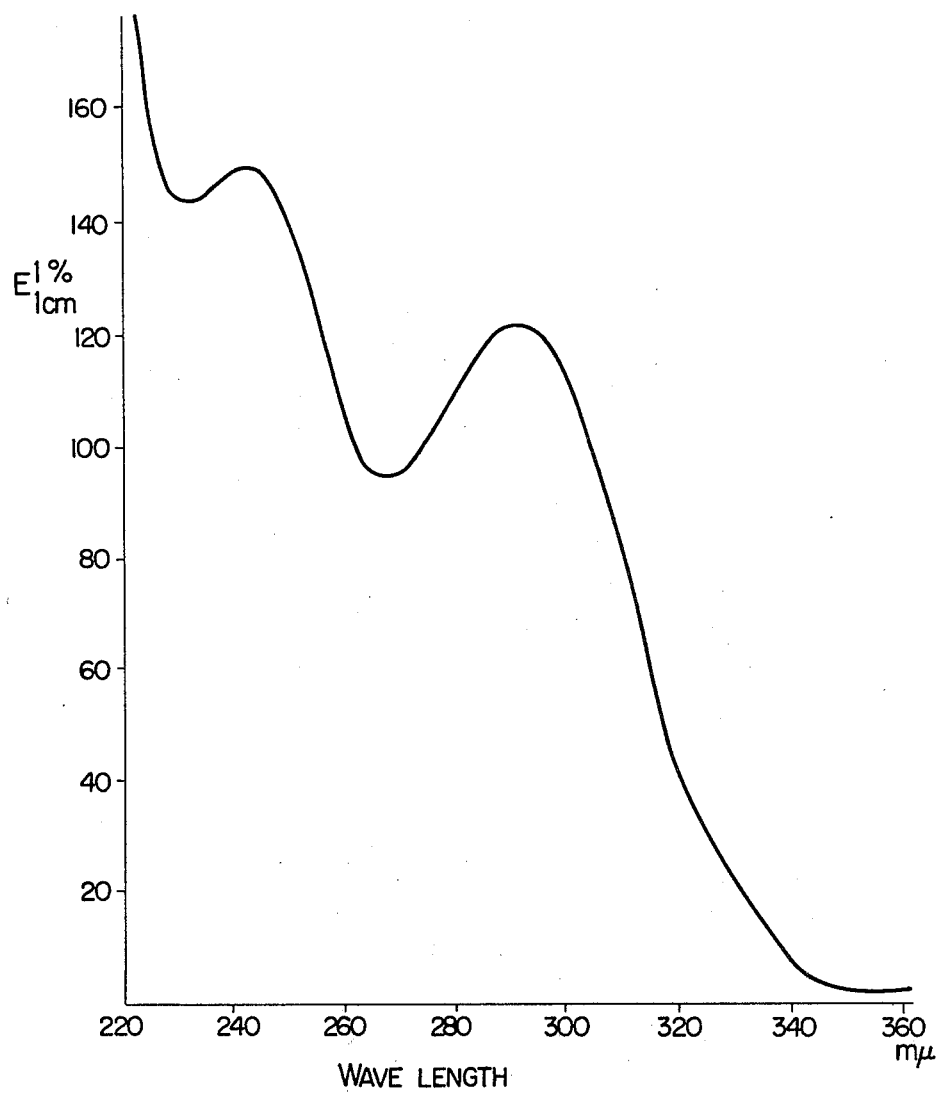
Figure 12:
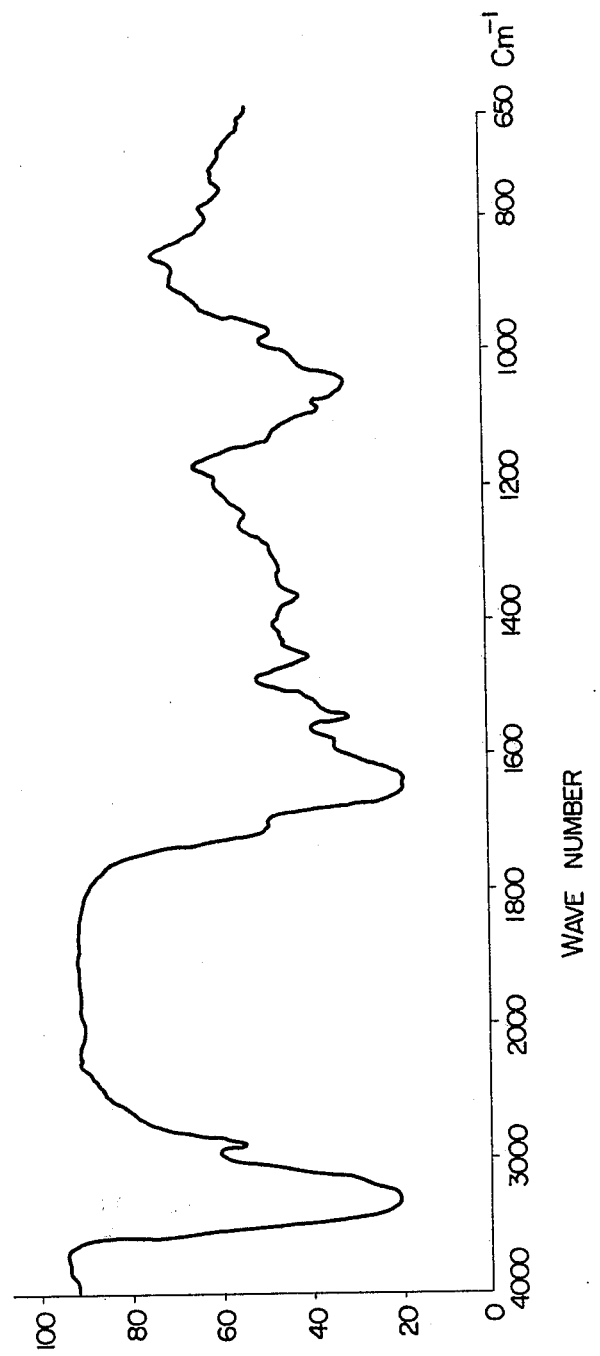

Step A: In 20 ml of dimethylformaldehyde, was dissolved 400 mg of N-methylbleomycinic acid (copper complex). To the solution, while being stirred at 23° C., were added 116 mg of N-methylmorpholine and 298 mg of CCBT. The mixture was stirred for 5 minutes, admixed with 166 mg of 3-aminoprophyldimethylsulfonium chloride (hydrochloride), allowed to react for 3 hours, and the reaction was terminated by adding 5.3 ml of glacial acetic acid. The reaction mixture was admixed with 300 ml of acetone to precipitate the intended product. The precipitate was dissolved in 10 ml of distilled water and treated as in Example 1 in the following manner. After desalting by using Amberlite ® XAD-2, the solution was subjected to the CM-Sephadex ® C-25 column chromatography to collect the eluate fraction at about 0.65 M. The fraction was desalted and lyophilized to obtain 369 mg (82% yield) of N-methylbleomycin $A_2$ (copper complex) hydrochloride in the form of bluish purple amorphous powder. The ultraviolet absorption spectrum, as measured in distilled water, and the infrared absorption spectrum of the powder taken by the potassium bromide tablet method, were as shown in FIGS. 8 and 12, respectively. The ultraviolet absorption maxima ($E_{1cm}^{1\%}$, distilled water) were at 292 (122) and 244 (148) mμ. Other physical and chemical properties were as shown in Table 1.

Figure 9:
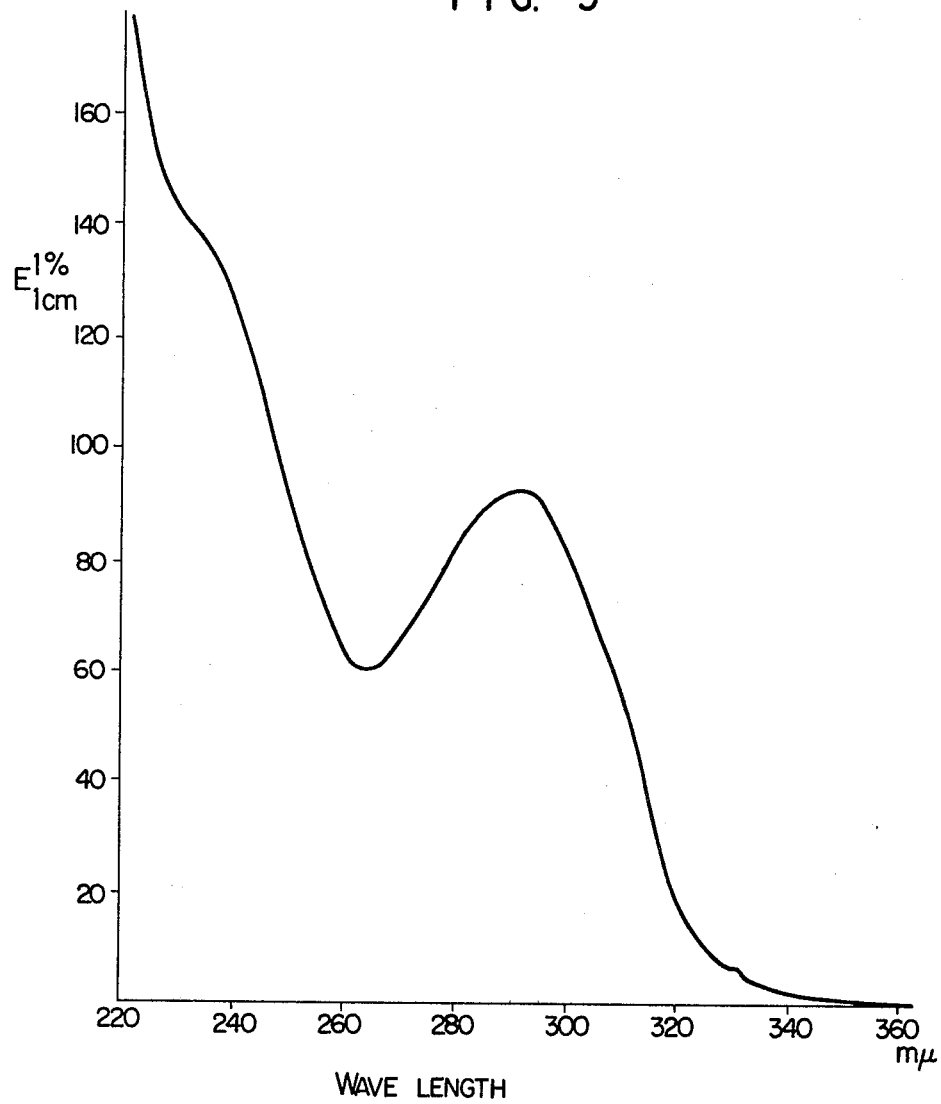
Figure 13:
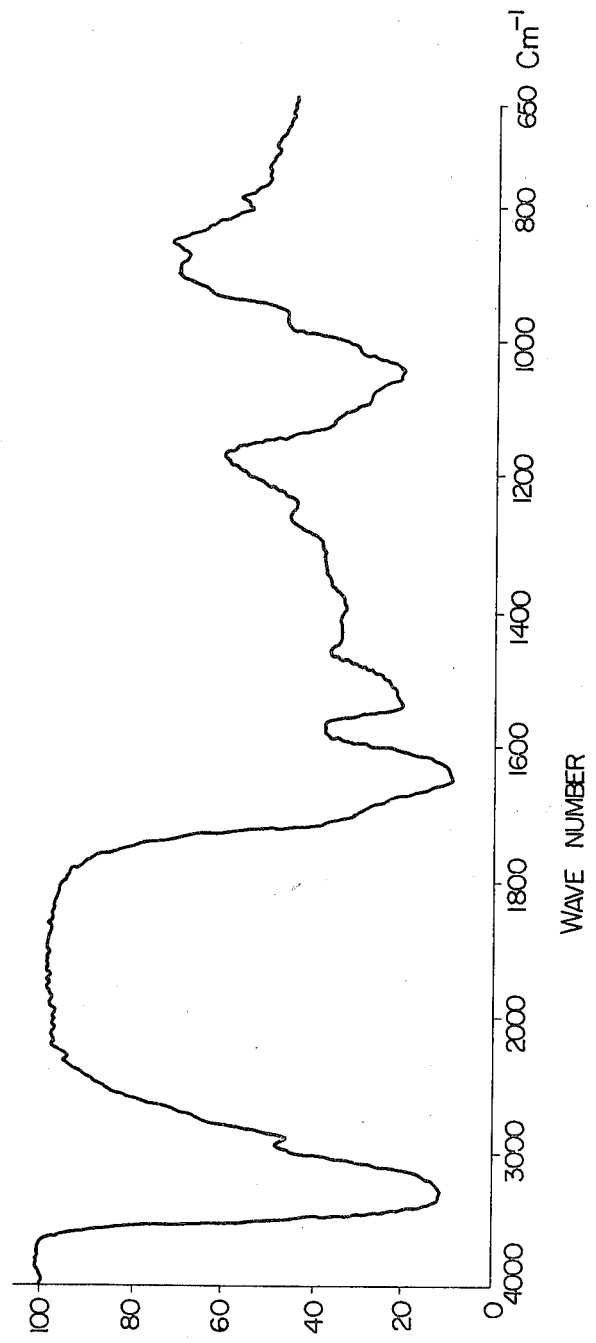

Step B: In 10 ml of distilled water, was dissolved 300 mg of the copper complex obtained in Step A. For the purpose of copper removal, the resulting solution was charged to an Amberlite ® XAD-2 column (200 ml) to effect adsorption. The column was washed successively with 600 ml of an aqueous solution containing 2% of sodium chloride and 5% of EDTA.Na₂, 400 ml of 2% aqueous sodium chloride solution, and 250 ml of distilled water. The adsorbed phase was eluted with a N/50 hydrochloric acid-methanol (1:4 V/V) mixture to collect a fraction having an absorption maximum at a wavelength of about 290 mμ. The collected fraction was adjusted to pH 6.0 with Dowex ® 44 (OH⁻ type), concentrated under reduced pressure, and lyophilized to obtain 265 mg (92% yield) of N-methylbleomycin $A_2$ (copper-free) hydrochloride in the form of white amorphous powder. The ultraviolet absorption spectrum and the infrared absorption spectrum of the powder taken by the potassium bromide tablet method, were as shown in FIGS. 9 and 13, respectively. The ultraviolet absorption maximum ($E_{1cm}^{1\%}$, distilled water) was at 291 (93) mμ. Other physical and chemical properties were as shown in Table 2.

EXAMPLE 5

Synthesis of N-methylbleomycin $B_2$

Step A: In 20 ml of dimethyl sulfoxide, was dissolved 400 mg of N-methylbleomycinic acid (copper complex). To the solution, while being stirred at 23° C., were added 116 mg of N-methylmorpholine and 298 mg of CCBT. The mixture was stirred for 5 minutes, admixed with 176 mg of agmatine (hydrochloride), and allowed to react for further 3 hours. The reaction mixture was treated in a manner similar to that of step A of example 4 to obtain 345 mg (76% yield) of N-methylbleomycin $B_2$ (copper complex) in the form of bluish purple amorphous powder. The ultraviolet absorption maxima ($E_{1cm}^{1\%}$, distilled water) were at 292 (123) and 244 (153) mμ. Other physical and chemical properties were as shown in Table 1.

Figure 10:
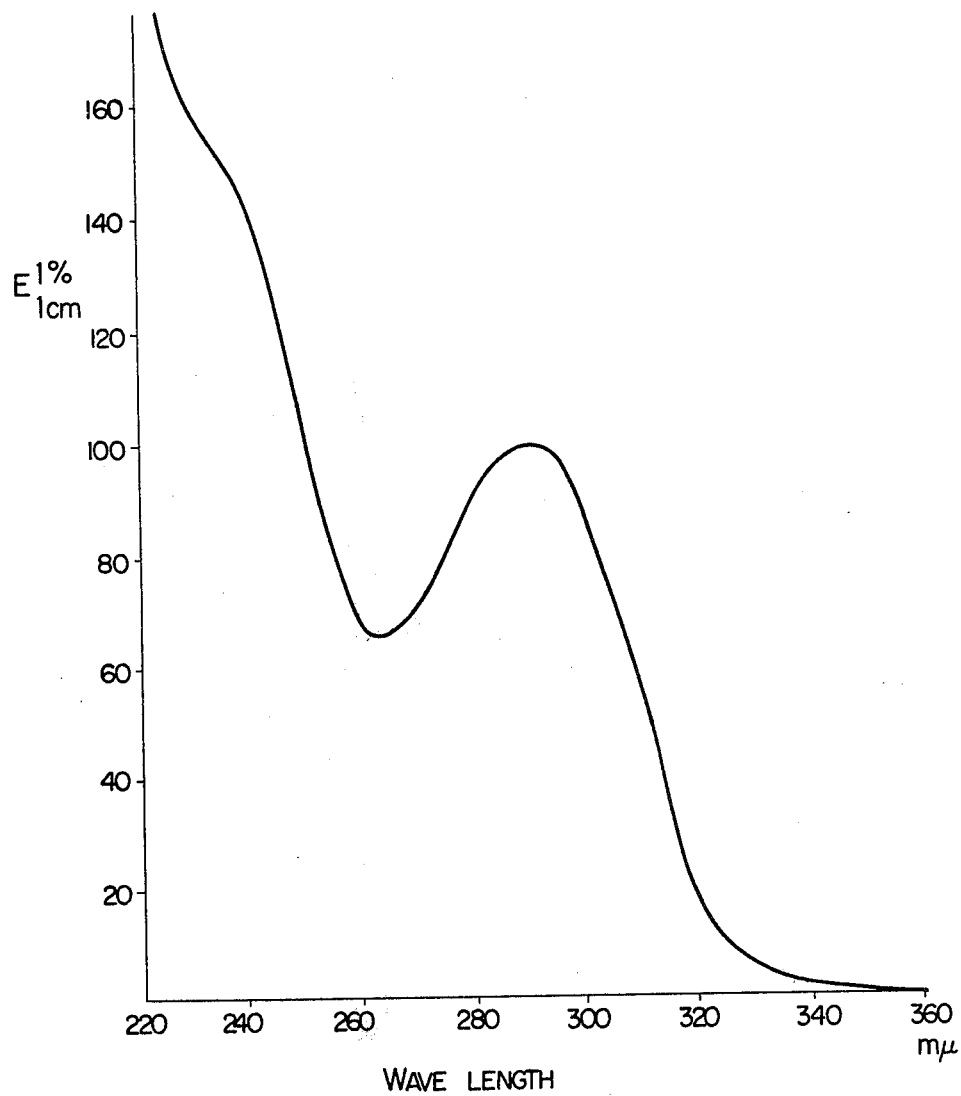
Figure 14:
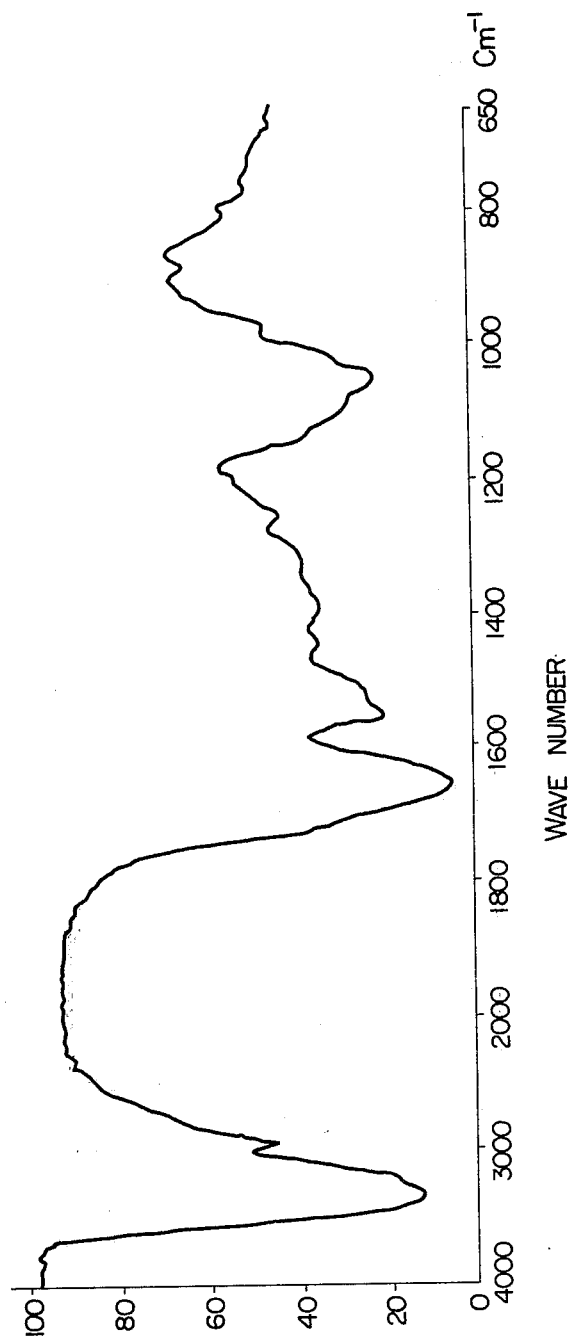

Step B: In a manner similar to that in step B of Example 4, 335 mg of the copper complex obtained in step A was freed from copper to obtain 280 mg (86% yield) of N-methylbleomycin $B_2$ (copper-free) hydrochloride in the form of white amorphous powder. The ultraviolet absorption spectrum, as measured in distilled water, and the infrared absorption spectrum taken by the method of potassium bromide tablet, were as shown in FIGS. 10 and 14, respectively. The ultraviolet absorption maximum ($E_{1cm}^{1\%}$, distilled water) was at 290 (101) mμ. Other physical and chemical properties were as shown in Table 2.

EXAMPLE 6

Synthesis of N-methylbleomycin $A_2'$-b

Step A: In 20 ml of dimethylformamide, was dissolved 400 mg of N-methylbleomycinic acid (copper complex). To the solution, while being stirred at 0° C., were added 29 mg of N-methylmorpholine and 298 mg of CCBT. The mixture was stirred for 5 minutes, admixed with 64 mg of 1,3-diaminopropane, and allowed to react for further 5 hours. The reaction mixture was treated in a manner similar to that of step A of Example 4 to obtain 402 mg (92% yield) of N-methylbleomycin $A_2'$-b (copper complex) hydrochloride in the form of bluish purple amorphous powder. The ultraviolet absorption maxima ($E_{1cm}^{1\%}$, distilled water) were at 292 (122) and 244 (148) mμ. Other physical and chemical properties were as shown in Table 3.

Step B: In a manner similar to that in step B of Example 4, 390 mg of the copper complex was freed from copper to obtain 333 mg (89% yield) of N-methylbleomycin $A_2'$-b (copper-free) hydrochloride in the form of white amorphous powder. The ultraviolet absorption maximum ($E_{1cm}^{1\%}$, distilled water) was at 291 (101) mμ.

EXAMPLE 7

Synthesis of 3-[(S)-1'-phenylethylamino]propylamino-N-methylbleomycin

Step A: In 20 ml of dimethylformamide, was dissolved 400 mg of N-methylbleomycinic acid (copper complex). To the solution, while being stirred at 27° C., were added 29 mg of N-methylmorpholine and 298 mg of CCBT. The mixture was stirred for 5 minutes, admixed with 154 mg of N-[(S)-1'-phenylethyl]-1,3-diaminopropane, and allowed to react for further 3 hours. In a manner similar to that in step A of Example 4, the reaction mixture was treated to obtain 304 mg (65% yield) of 3-[(S)-1'-phenylethylamino]propylamino-N-methylbleomycin (copper complex) hydrochloride in the form of bluish purple amorphous powder. The ultraviolet absorption maxima of the powder ($E_{1cm}^{1\%}$, distilled water) were at 292 (114) and 243 (140) mμ.

Step B: In a manner similar to that in step B of Example 4, 290 mg of the copper complex obtained in step A was freed from copper to obtain 257 mg (92% yield) of 3-[(S)-1'-phenylethylamino]propylamino-N-methylbleomycin (copper-free) hydrochloride in the form of white amorphous powder. The ultraviolet absorption maximum ($E_{1cm}^{1\%}$, distilled water) was at 290 (101) m$\mu$.

EXAMPLE 8

Synthesis of 3-(3-n-butylaminopropylamino)propylamino-N-methylbleomycin

Step A: In 20 ml of dimethylformamide, was dissolved 400 mg of N-methylbleomycinic acid (copper complex). To the solution, while being stirred at 0° C., were added 29 mg of N-methylmorpholine and 298 mg of CCBT. The mixture was stirred for 5 minutes, admixed with 162 mg of N-3-aminopropyl-N'-n-butyl-1,3-diaminopropane, and allowed to react for further one hour. The reaction mixture was treated in a manner similar to that in step A of Example 4 (however, the fraction eluted from the CM-Sephadex C-25 column at a concentration of about 0.80 M was collected) to obtain 246 mg (51% yield) of 3-(3-n-butylaminopropylamino)-propylamino-N-methylbleomycin (copper complex) in the form of bluish purple amorphous powder. The ultraviolet absorption maxima ($E_{1cm}^{1\%}$, distilled water) were at 292 (102) and 243 (125) m$\mu$.

Step B: In a manner similar to that in step B of Example 4, 237 mg of the copper complex obtained in step A was freed from copper to obtain 194 mg (85% yield) of 3-(3-n-butylaminopropylamino)propylamino-N-methylbleomycin (copper-free) hydrochloride in the form of white amorphous powder. The ultraviolet absorption maximum ($E_{1cm}^{1\%}$, distilled water) was at 290 (99) m$\mu$.

EXAMPLE 9

Synthesis of N-methylbleomycin $A_2$

Step A: In 70 ml of methanol, was dissolved 1.0 g of bleomycin $A_2$ (copper-free) hydrochloride. To the solution, while being stirred at 25° C., were added an aqueous solution containing 30 mg of formaldehyde, followed by 29 mg of sodium cyanoborohydride. After 16 hours of reaction, the reaction system was adjusted to pH 1.0 with 1 N hydrochloric acid to terminate the reaction after 10 minutes of standing. The reaction mixture was neutralized with 1 N sodium hydroxide solution, freed from methanol by distillation under reduced pressure, and the residue was made up to 10 ml with distilled water. For the purpose of desalting, the resulting solution was fed to a column packed with 300 ml of Amberlite ® XAD-2 with distilled water to absorb the intended product. After washing with distilled water, the column was eluted with a N/50 hydrochloric acid-methanol (1:4 V/V) mixture, and a fraction having an absorption maximum at wavelengths around 290 m$\mu$ was collected. The fraction was neutralized with an anion exhange resin Dowex ® 44 (OH⁻ type), concentrated under reduced pressure, and then lyophilized to obtain a crude product in the form of powder.

The crude product was dissolved in 10 ml of distilled water, admixed with 113 mg of basic cupric carbonate, and stirred at room temperature for 2 hours. The excess basic cupric carbonate was removed by filtration, and the resulting bluish purple filtrate was charged to a column packed with 200 ml of CM-Sephadex ® C-25 (Na⁺ type) which had been equilibrated with N/20 acetic acid-sodium acetate buffer of pH 4.5 to adsorb the intended product. The column was eluted by the linear gradient method by as eluent 2 liters of the said buffer solution to which was added continuously sodium chloride to increase gradually the sodium chloride concentration up to 1.0 without changing the pH. An effluent fraction, bluish purple in color, at a sodium chloride concentration of about 0.65 M was collected. In order to improve the purity, the above column chromatography was repeated and then the intended fraction was desalted by means of a desalting method using Amberlite ® XAD-2 as mentioned above. The fraction thus treated was concentrated under reduced pressure and then lyophilized to obtain 446 mg (42% yield) of N-methylbleomycin $A_2$ (copper complex) hydrochloride in the form of bluish purple amorphous powder.

The ultraviolet absorption spectrum and antimicrobial activity of the powder were as follows:

Ultraviolet absorption maxima ($E_{1cm}^{1\%}$, distilled water): 292 (122), 244 (148) m$\mu$.

Antimicrobial activity: 520 mcg units/mg.

Note: Antimicrobial activity was assayed against *Mycobacterium smegmatis* ATCC 607 by assuming the activity of bleomycin $A_2$ (copper-free form) to be 1,000 mcg units/mg. The same shall apply hereinafter.

Step B: In 10 ml of distilled water, was dissolved 430 mg of the copper complex obtained in step A. For the purpose of copper removal, the resulting sulution was charged to an Amberlite ® XAD-2 column (200 ml volume) to effect adsorption. The column was washed successively with 600 ml of an aqueous solution containing 2% of sodium chloride and 5% of EDTA.Na₂, 400 ml of 2% aqueous sodium chloride solution and 250 ml of distilled water. The adsorbed phase was eluted with N/50 hydrochloric acid-methanol (1:4 V/V) mixture to collect a fraction having an absorption maximum at about 290 m$\mu$. The collected fraction was adjusted to pH 6.0 with Dowex ® 44 (OH⁻ type), concentrated under reduced pressure, and lyophilized to obtain 380 mg (92% yield) of N-methylbleomycin $A_2$ (copper-free) hydrochloride in the form of white amorphous powder. The ultraviolet absorption spectrum and the antimicrobial activity of this product were as follows:

Ultraviolet absorption maximum ($E_{1cm}^{1\%}$, distilled water): 291 (93) m$\mu$.

Antimicrobial activity: 418 mcg units/mg.

EXAMPLE 10

Synthesis of N-methylbleomycin $A_2$

Step A: In 70 ml of methanol, was dissolved 1.0 g of bleomycin $A_2$ (copper-free) hydrochloride. To the solution, while being stirred at 0° C., were added an aqueous solution containing 25 mg of formaldehyde, followed by 29 mg of sodium cyanoborohydride. After 24 hours reaction, the reaction system was adjusted to pH 1.0 to terminate the reaction.

The reaction mixture was treated in a manner similar to that in step A of Example 9 to obtain 191 mg (18% yield) of N-methylbleomycin $A_2$ (copper complex) hydrochloride in the form of bluish purple amorphous powder.

The ultraviolet absorption spectrum and atnimicrobial activity of the powder were as follows:

Ultraviolet absorption maximam ($E_{1cm}^{1\%}$, distilled water): 292 (122), 244 (148) m$\mu$.

Antimicrobial activity: 516 mcg units/mg.

Step B: In a manner similar to that in step B of Example 9, 180 mg of the copper complex obtained in step A was freed from copper to obtain 157 mg of N-methylbleomycin $A_2$ (copper-free) hydrochloride in the form of white amorphous powder.

The ultraviolet absorption maximum and antimicrobial activity of the powder were as follows:

Ultraviolet absorption maximum ($E_{1cm}^{1\%}$, distilled water): 291 (93) mµ.

Antimicrobial activity: 427 mcg units/mg.

EXAMPLE 11

Synthesis of N-methylbleomycin $A_2$

Step A: In 70 ml of methanol, was dissolved 1.0 g of bleomycin $A_2$ (copper-free) hydrochloride. To the solution, while being stirred at 30° C., were added an aqueous solution containing 25 mg of formaldehyde, followed by 29 mg of sodium cyanoborohydride. After 10 hours reaction, the reaction system was adjusted to pH 1.0 to terminate the reaction. In a manner similar to that in step A of Example 9, the reaction mixture was treated to obtain 209 mg (20% yield) of N-methylbleomycin $A_2$ (copper complex) hydrochloride in the form of bluish purple amorphous powder. The ultraviolet absorption spectrum of the powder and anti-microbial activity were as follows:

Ultraviolet absorption maximum ($E_{1cm}^{1\%}$, distilled water): 292 (122), 244 (148) mµ.

Antimicrobial activity: 507 mcg units/mg.

Step B: In a manner similar to that in step B of Example 9, 200 mg of the copper complex obtained in step A was freed from copper to obtain 173 mg (90% yield) of N-methylbleomycin $A_2$ (copper-free) hydrochloride in the form of white amorphous powder.

The ultraviolet absorption spectrum and antimicrobial activity of the powder were as follows:

Ultraviolet absorption maximum ($E_{1cm}^{1\%}$, distilled water): 291 (93) mµ.

Antimicrobial activity: 420 mcg units/mg.

EXAMPLE 12

Synthesis of N-methylbleomycin $B_2$

Step A: In 60 ml of methanol, was dissolved 1.0 g of bleomycin $B_2$ (copper-free) hydrochloride. To the solution, while being stirred at 25° C., were added an aqueous solution containing 23 mg of formaldehyde, followed by 32 mg of sodium cyanoborohydride. After 16 hours reaction, the reaction system was adjusted to pH 1.0 to terminate the reaction. In a manner similar to that in step A of Example 9, the reaction mixture was treated to obtain 385 mg (37% yield) of N-methylbleomycin $B_2$ (copper complex) hydrochloride in the form of bluish purple amorphous powder.

The ultravioled absorption spectrum and antimicrobial activity were as follows:

Ultraviolet absorption maximum ($E_{1cm}^{1\%}$, distilled water): 292 (123), 244 (153) mµ.

Antimicrobial activity: 1,758 mcg units/mg.

Step B: In a manner similar to that in step B of Example 9, 375 mg of the copper complex obtained in step A was freed from copper to obtain 335 mg (93% yield) of N-methylbleomycin $B_2$ (copper-free) hydrochloride in the form of white amorphous powder.

The ultraviolet absorption spectrum and antimicrobial activity were as follows:

Ultraviolet absorption maximum ($E_{1cm}^{1\%}$, distilled water): 290 (101) mµ.

Antimicrobial activity: 1,752 mcg units/mg.

EXAMPLE 13

Synthesis of N-methylbleomycin $B_2$

Step A: In 70 ml of methanol, was dissolved 1.0 g of bleomycin $B_2$ (copper-free) hydrochloride. To the solution, while being stirred at 25° C., were added an aqueous solution containing 30 mg of formaldehyde, followed by 63 mg of sodium cyanoborohydride. After 2 hours reaction, the reaction system was adjusted to pH 1.0 to terminate the reaction.

In a manner similar to that in step A of Example 9, the reaction mixture was treated to obtain 168 mg (16% yield) of N-methylbleomycin $B_2$ (copper complex) hydrochloride in the form of bluish purple amorphous powder.

The ultraviolet absorption spectrum and antimicrobial activity of the powder were as follows:

Ultraviolet absorption maximum ($E_{1cm}^{1\%}$, distilled water): 292 (123), 244 (153) mµ.

Antimicrobial activity: 1,770 mcg units/mg.

Step B: In a manner similar to that in step B of Example 9, 150 mg of the copper complex obtained in step A was freed from copper to obtain 127 mg (88% yield) of N-methylbleomycin $B_2$ (copper-free) hydrochloride in the form of white amorphous powder.

The ultraviolet absorption spectrum and antimicrobial activity of the power were as follows:

Ultraviolet absorption maximum ($E_{1cm}^{1\%}$, distilled water): 290 (101) mµ.

Antimicrobial activity: 1,756 mcg units/mg.

EXAMPLE 14

Synthesis of 3-[(S)-1'-phenylethylamino]propylamino-N-methylbleomycin

Step A: In 100 ml of methanol, was dissolved 1.0 g of 3-[(S)-1'-phenylethylamino]propylaminobleomycin (copper-free) hydrochloride. To the solution, while being stirred at 25° C., were added an aqueous solution containing 19 mg of formaldehyde, followed by 41 mg of sodium cyanoborohydride. After 6 hours reaction, the reaction system was adjusted to pH 1.0 to terminate the reaction.

In a manner similar to that in step A of Example 9, the reaction mixture was treated to obtain 86 mg (8.2% yield) of 3-[(S)-1'-phenylethylamino]propylamino-N-methylbleomycin (copper complex) hydrochloride in the form of bluish purple amorphous powder.

The ultraviolet absorption spectrum and antimicrobial activity of the powder were as follows:

Ultraviolet absorption maximum ($E_{1cm}^{1\%}$, distilled water): 292 (114), 243 (140) mµ.

Antimicrobial activity: 4,320 mcg units/mg.

Step B: In a manner similar to that in step B of Example 9, 80 mg of the copper complex obtained in step A was freed from copper to obtain 74 mg (96% yield) of 3-[(S)-1'-phenylethylamino]propylamino-N-methylbleomycin (copper-free) hydrochloride in the form of white amorphous powder.

The ultraviolet absorption spectrum and antimicrobial activity of the powder were as follows:

Ultraviolet absorption maximum ($E_{1cm}^{1\%}$, distilled water): 290 (101) mµ.

Antimicrobial activity: 4,280 mcg units/mg.

EXAMPLE 15

Synthesis of 3-(tert-butoxycarbonylamino)propylamino-N-methylbleomycin

Step A: In 75 ml of methanol, was dissolved 1.0 g of 3-(tert-butoxycarbonylamino)propylaminobleomycin (copper-free) hydrochloride. To the solution, while being stirred at 27° C., were added an aqueous solution containing 20 mg of formaldehyde, followed by 55 mg of sodium cyanoborohydride. After 14 hours reaction, the reaction system was adjusted to pH 1.0 to terminate the reaction.

In a manner similar to that in step A of Example 9, the reaction mixture was treated, except that a fraction at around 0.50 M of CM-Sephadex chromatography was collected. As the result, 335 mg (32% yield) of the intended product (copper complex) hydrochloride in the form of bluish purple amorphous powder was obtained.

The ultraviolet absorption maximum of the powder ($E_{1cm}^{1\%}$, distilled water) were at 292 (117) and 243 (147) mμ.

Step B: In a manner similar to that in step B of Example 9, 325 mg of the copper complex obtained in step A was freed from copper to obtain 269 mg (86% yield) of the intended product (copper-free) hydrochloride in the form of white amorphous powder.

The Ultraviolet absorption maximum of the powder ($E_{1cm}^{1\%}$, distilled water) was 291 (100) mμ.

Reference Example 1

Tert-Butoxycarbonization of 3-aminopropylaminobleomycin

In 4 ml of distilled water, was dissolved 750 mg of 3-aminopropylaminobleomycin (copper complex) hydrochloride. To the solution, while being stirred at 23° C., were added 0.3 ml of triethylamine and 134 mg of 2-(tert-butoxycarbonylthio)-4,6-dimethylpyrimidine in the form of dioxane solution. After 12 hours reaction, 200 ml of acetone was added to the reaction mixture to precipitate the product. The precipitates were dissolved in 20 ml of distilled water, and the solution was neutralized with 1 N hydrochloric acid. Thereafter, the product was freed from copper in a manner similar to that in step B of Example 9 of obtain 558 mg (78% yield) of 3-(tert-butoxycarbonylamino)propylaminobleomycin (copper-free) hydrochloride in the form of white amorphous powder.

The ultraviolet absorption maximum of the powder ($E_{1cm}^{1\%}$, distilled water) was 291 (101) mμ.

Reference Example 2

Removal of tertiary-butoxycarbonyl group from 3-(tert-butoxycarbonylamino)propylamino-N-methylbleomycin In 3.6 ml of distilled water, was dissolved 80 mg of 3-(tert-butoxycarbonylamino)propylamino-N-methylbleomycin (copper complex) hydrochloride. To the solution, was added 2.4 ml of trifluoroacetic acid. After the reaction was carried out at 23° C. for 1 hour, trifluoroacetic acid was removed by distillation under reduced pressure. The residue was neutralized with 1 N sodium hydroxide. In a manner similar to that in step B of Example 9, the residue was freed from copper to obtain 48 mg (63% yield) of 3-aminopropylamino-N-methylbleomycin (copper-free) hydrochloride in the form of white amorphous powder.

The ultraviolet absorption maximum ($E_{1cm}^{1\%}$, distilled water) and antimicrobial activity of the powder were 291 (101) mμ and 618 mcg units/mg, respectively.

What is claimed is:

1. A N-methylbleomycin represented by the general formula

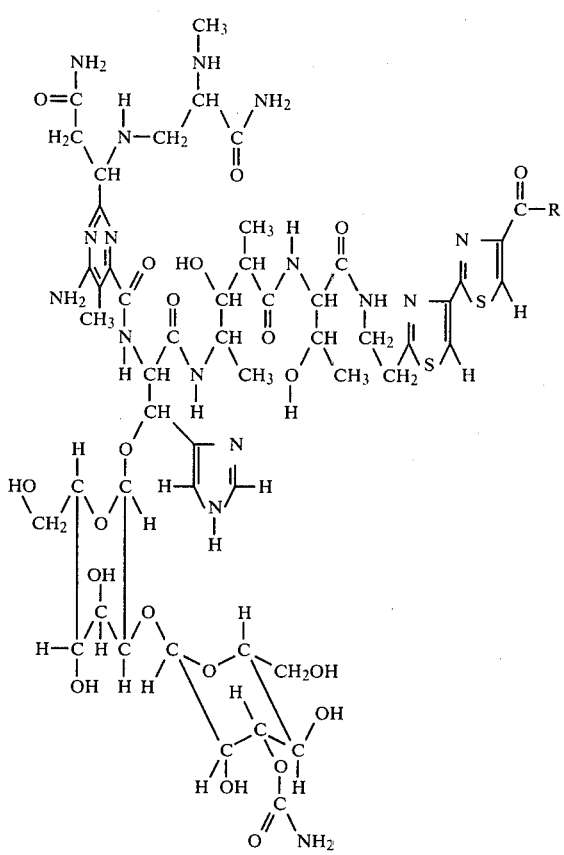

(wherein R represents a terminal amine moiety of bleomycins), a copper complex thereof, and a non-toxic salt thereof.

2. A compound according to claim 1, wherein R is dialkyl($C_1$-$C_3$)sulfoniumalkyl($C_2$-$C_5$)amino, guanidinoalkyl($C_2$-$C_5$)amino, aminoalkyl($C_2$-$C_5$)amino, phenylalkyl($C_1$-$C_4$)aminoalkyl($C_2$-$C_5$)amino or alkyl(-$C_2$-$C_5$)aminoalkyl($C_2$-$C_5$)aminoalkyl($C_2$-$C_5$)amino.

3. A compound according to claim 2, wherein R is 3-[(S)-1-phenylethylamino]propylamino.

4. A compound according to claim 2, wherein R is 3-(3-n-butylaminopropylamino)propylamino.

5. A compound according to claim 2, wherein R is

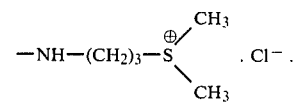

6. A compound according to claim 2, wherein R is guanidinobutylamino.

7. A compound according to claim 2, wherein R is aminopropylamino.

8. N-Methylbleomycinic acid represented by the following formula,

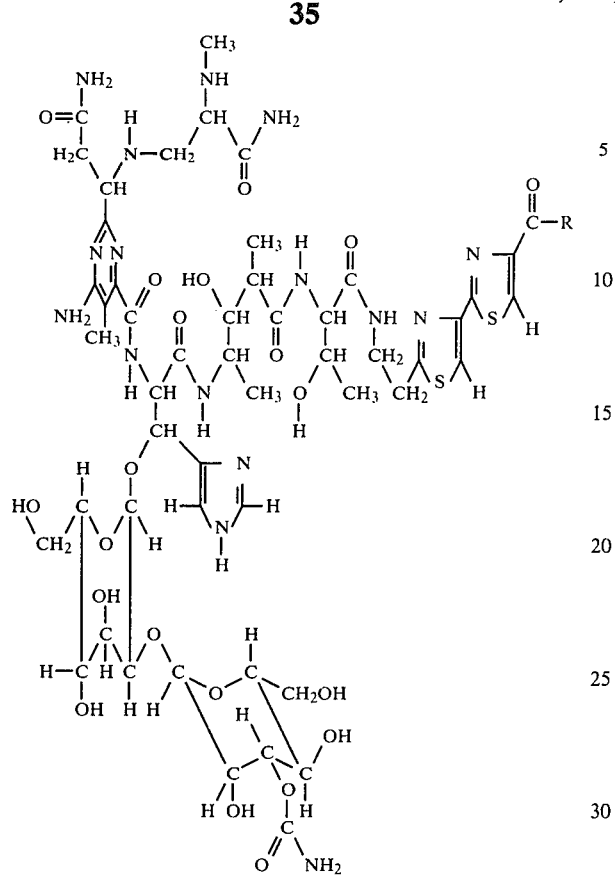

United States Patent [19]

Cohen

[11] 4,267,103

[45] May 12, 1981

[54] SOLVENT POLYMERIZATION OF CARBOXYL CONTAINING MONOMERS

[75] Inventor: Louis Cohen, Avon Lake, Ohio

[73] Assignee: The B. F. Goodrich Company, Akron, Ohio

[21] Appl. No.: 967,447

[22] Filed: Dec. 7, 1978

[51] Int. Cl.³ .......................... C08F 2/06; C08L 1/02; C08L 1/00

[52] U.S. Cl. .................... 260/17.4 UC; 260/17.4 SG; 526/208; 526/209; 526/212; 526/216; 526/240; 526/303; 526/317; 526/923

[58] Field of Search ............... 526/240, 317, 208, 209, 526/216, 303, 923, 212; 260/17.4 UC, 17.4 SG

[56] References Cited

U.S. PATENT DOCUMENTS

| | | | |
|---|---|---|---|
| 2,244,703 | 6/1941 | Hubbuch | 526/317 |
| 2,878,237 | 3/1959 | Russell et al. | 526/317 |
| 3,025,219 | 3/1962 | Maeder | 526/212 |
| 3,336,269 | 8/1967 | Monage et al. | 526/212 |
| 3,379,702 | 4/1968 | Spivey | 526/212 |
| 3,479,284 | 11/1969 | Lees | 526/212 |
| 3,509,113 | 4/1970 | Monagle et al. | 526/212 |
| 3,850,898 | 11/1974 | Ide et al. | 526/317 |
| 3,872,063 | 3/1975 | Kim | 526/240 |
| 3,919,140 | 11/1975 | Hirata | 526/216 |
| 3,970,633 | 7/1976 | Miller et al. | 526/240 |
| 4,028,290 | 6/1977 | Reid | 260/17.4 ST |
| 4,062,817 | 12/1977 | Westerman | 526/15 |
| 4,066,522 | 1/1978 | Machi et al. | 526/216 |
| 4,066,583 | 1/1978 | Spaulding | 260/17.4 SG |
| 4,158,726 | 6/1979 | Kamada et al. | 526/292 |
| 4,167,464 | 9/1979 | George | 526/240 |

OTHER PUBLICATIONS

Chem. Abs. 26363t, vol. 81, (1974), "Sparingly Cross-linked Acrylic Acid Copolymers", Naumov et al.

*Primary Examiner*—Joseph L. Schofer
*Assistant Examiner*—Herbert J. Lilling
*Attorney, Agent, or Firm*—J. Hughes Powell, Jr.

[57] ABSTRACT

Carboxyl or carboxyl salt containing polymers are prepared by polymerizing carboxyl containing monomers wherein greater than one percent of the carboxyl groups are neutralized with an alkali, ammonia or an amine, optionally copolymerized with other vinylidene monomers containing at least one terminal $CH_2{=}CH{<}$ group dissolved in a solvent for the monomers which is a non-solvent for the polymer with a free radical catalyst, so that the resulting polymer is obtained suspended as a fine, readily recoverable substantially non-swollen fine powder. The solvents used are moderately to strongly hydrogen bonded and have solubility parameters of from about 8 to 15.

24 Claims, No Drawings